United States Patent
Nanthakumar et al.

(10) Patent No.: US 9,662,178 B2
(45) Date of Patent: May 30, 2017

(54) SYSTEM AND METHOD FOR DECREMENT EVOKED POTENTIAL (DEEP) MAPPING TO IDENTIFY COMPONENTS OF THE ARRYTHMOGENIC CIRCUIT IN CARDIAC ARRHYTHMIAS

(71) Applicant: University Health Network, Toronto (CA)

(72) Inventors: Kumaraswamy Nanthakumar, Toronto (CA); Eugene Downar, Toronto (CA); Stephane Masse, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 14/891,843

(22) PCT Filed: May 16, 2014

(86) PCT No.: PCT/CA2014/000438
§ 371 (c)(1),
(2) Date: Nov. 17, 2015

(87) PCT Pub. No.: WO2014/183206
PCT Pub. Date: Nov. 20, 2014

(65) Prior Publication Data
US 2016/0128785 A1    May 12, 2016

Related U.S. Application Data
(60) Provisional application No. 61/824,457, filed on May 17, 2013.

(51) Int. Cl.
A61B 5/04 (2006.01)
A61B 34/10 (2016.01)
(Continued)

(52) U.S. Cl.
CPC .............. *A61B 34/10* (2016.02); *A61B 5/042* (2013.01); *A61B 5/0422* (2013.01);
(Continued)

(58) Field of Classification Search
CPC ... A61B 5/0452; A61B 5/0422; A61B 5/0464; A61B 5/0472
See application file for complete search history.

(56) References Cited

U.S. PATENT DOCUMENTS 5,579,764 A * 12/1996 Goldreyer ............ A61B 5/0422
600/374
7,966,067 B2    6/2011 Rousso et al.
(Continued)

FOREIGN PATENT DOCUMENTS

| EP | 2996554 A1 | 3/2016 |
|----|------------|--------|
| WO | 94/15528 A1 | 7/1994 |

(Continued)

OTHER PUBLICATIONS
International Search Report and Written Opinion in relation to corresponding application No. PCT/CA2014/000438, mailed on Aug. 13, 2014.
(Continued)

*Primary Examiner* — Robert N Wieland
(74) *Attorney, Agent, or Firm* — Bereskin & Parr LLP/S.E.N.C.R.L., s.r.l.; Tony Orsi

(57) ABSTRACT

Various embodiments are described herein for a system and a method for identifying the arrhythmogenic circuit of a patient or subject. In one embodiment, the method comprises obtaining data for electrograms recorded at various locations of the heart while programmed ventricular pacing with extra stimuli was performed, obtaining decrement values for at least two different locations of the heart using the recorded electrograms, generating at least a portion of a (Continued)

decrement map using the decrement values, and identifying the arrhythmogenic circuit based on electrograms having significant decremental properties.

24 Claims, 15 Drawing Sheets

(51) Int. Cl.
    A61B 5/042      (2006.01)
    A61B 5/0472    (2006.01)
    A61B 5/0464    (2006.01)
    A61B 5/0452    (2006.01)
    A61B 5/00       (2006.01)

(52) U.S. Cl.
    CPC .......... *A61B 5/0464* (2013.01); *A61B 5/0472* (2013.01); *A61B 5/6852* (2013.01); *A61B 5/0452* (2013.01); *A61B 5/686* (2013.01); *A61B 5/6869* (2013.01); *A61B 2034/105* (2016.02); *A61B 2505/05* (2013.01)

(56) References Cited

U.S. PATENT DOCUMENTS

| | | | |
|---|---|---|---|
| 8,239,019 B2 | 8/2012 | Dorr et al. | |
| 2002/0065459 A1* | 5/2002 | MacAdam | A61B 5/042 600/424 |
| 2003/0023130 A1 | 1/2003 | Ciaccio | |
| 2016/0166166 A1* | 6/2016 | Bunch | A61B 5/046 600/518 |

FOREIGN PATENT DOCUMENTS

| | | |
|---|---|---|
| WO | 2005/006946 A2 | 1/2005 |
| WO | 2008063498 A1 | 5/2008 |
| WO | 2014183206 A1 | 11/2014 |

OTHER PUBLICATIONS

S. Masse, E. Sevaptsidis, I.D. Parson, S. Kimber, and E. Downar, "A Data Acquisition System for Real-Time Activation Detection of Cardiac Electrograms II: Software", submitted to the 13th Annual International Conference of the IEEE Engineering in Medicine and Biology Society, 1991, vol. 13, pp. 782-783.
Almendral JM, Gottlieb CD, Rosenthal ME, Stamato NJ, Buxton AE, Marchlinski FE, Miller JM, Josephson ME: Entrainment of ventricular tachycardia: explanation for surface electrocardiographic phenomena by analysis of electrograms recorded within the tachycardia circuit. Circulation 1988, 77(3), pp. 569-580.
D. Durrer, R.Th. Van Dam, G.E Freud, M.J. Janse, F.L Meijler, and R.C. Arzbaecher, "Total Excitation of the Isolated Heart", Circulation, vol. 16, pp. 899-912, 1970.
El-Shalakany A, Hadjis T, Papageorgiou P, Monahan K, Epstein L, Josephson ME: Entrainment/mapping criteria for the prediction of termination of ventricular tachycardia by single radiofrequency lesion in patients with coronary artery disease. Circulation 1999, 99(17), pp. 2283-2289.
I.D. Parson, P. Mendler, and E. Downar, "On-Line Cardiac Mapping: An Analog Approach using Video and Multiplexing Techniques", Am. J. Physiol., No. 242, pp. H526-H535, 1982.
R.E. Ideker, W.M. Smith, P. Wolf, N.D. Danieley, and F.R. Bartram, "Simultaneous Multichannel Cardiac Mapping Systems", Pace, vol. 10, pp. 281-292, 1987.
S. Masse, E. Sevaptsidis, I.D. Parson, S. Kimber, and E. Downar, "A Data Acquisition System for Real-Time Activation Detection of Cardiac Electrograms I: Hardware", submitted to the 13th Annual International Conference of the IEEE Engineering in Medicine and Biology Society, 1991, pp. 780-781.

S.M. Blanchard, W.M. Smith, R.J. Damiano, D.W. Molter, R.E. Ideker, and J.E. Lowe, "Four Digital Algorithms for Activation Detection from Unipolar Epicardial Electrograms", IEEE Trans. Biomed. Eng., vol. BME-36, No. 2, pp. 256-261, 1989.
C. Cabo, J.M. Wharton, R.E Ideker and W.M. Smith, "Digital Filters for Activation Detection in Unipolar Cardiac Electrograms", 10th Annual International Conference of the IEEE Engineering in Medicine and Biology Society, p. 0110, 1988.
E.V. Simpson, R.E Ideker and W.M. Smith, "An Automatic Activation Detector for Bipolar Cardiac Electrograms", 10th Annual International Conference of the IEEE Engineering in Medicine & Biology Society, p. 0113, 1988.
I.D. Parson and E. Downar, "Cardiac Mapping Instrumentation for the Instantaneous Display of Endocardial and Epicardial Activation", IEEE Trans. Biomed. Eng., vol. BME-34, No. 6, pp. 468-472, 1987.
Natale A, Raviele A, Al-Ahmad A, Alfieri O, Aliot E, Almendral J, Breithardt G, Brugada J, Calkins H, Callans D et al: Venice Chart International Consensus document on ventricular tachycardia/ventricular fibrillation ablation. J Cardiovasc Electrophysiol 2010, 21(3), pp. 339-379.
Arenal A, Hernandez J, Calvo D, Ceballos C, Atea L, Datino T, Atienza F, Gonzalez-Torrecilla E, Eidelman G, Miracle A et al: Safety, long-term results, and predictors of recurrence after complete endocardial ventricular tachycardia substrate ablation in patients with previous myocardial infarction. Am J Cardiol 2013, 111(4), pp. 499-505.
Kottkamp H, Wetzel U, Schirdewahn P, Dorszewski A, Gerds-Li JH, Carbucicchio C, Kobza R, Hindricks G: Catheter ablation of ventricular tachycardia in remote myocardial infarction: substrate description guiding placement of individual inear lesions targeting noninducibility. J Cardiovasc Electrophysiol 2003, 14(7), pp. 675-681.
Jais P, Maury P, Khairy P, Sacher F, Nault I, Komatsu Y, Hocini M, Forclaz A, Jadidi AS, Weerasooryia R et al: Elimination of local abnormal ventricular activities: a new end point for substrate modification in patients with scar-related ventricular tachycardia. Circulation 2012, 125(18), pp. 2184-2196.
Arenal A, Glez-Torrecilla E, Ortiz M, Villacastin J, Fdez-Portales J, Sousa E, del Castillo S, Perez de Isla L, Jimenez J, Almendral J: Ablation of electrograms with an isolated, delayed component as treatment of unmappable monomorphic ventricular tachycardias in patients with structural heart disease. J Am Coll Cardiol 2003, 41(1), pp. 81-92.
Yokokawa M, Desjardins B, Crawford T, Good E, Morady F, Bogun F: Reasons for recurrent ventricular tachycardia after catheter ablation of post-infarction ventricular tachycardia. J Am Coll Cardiol 2013, 61(1), pp. 66-73.
Yoshida K, Sekiguchi Y, Tanoue K, Endo M, Suzuki A, Kanemoto M, Yamasaki H, Yamauchi Y, Takahashi A, Kuga K et al: Feasibility of targeting catheter ablation to the markedly low-voltage area surrounding infarct scars in patients with post-infarction ventricular tachycardia. Circ J 2008, 72(7), pp. 1112-1119.
Mickleborough LL, Harris L, Downar E, Parson I, Gray G: A new intraoperative approach for endocardial mapping of ventricular tachycardia. J Thorac Cardiovasc Surg 1988, 95(2), pp. 271-280.
Tanner H, Hindricks G, Volkmer M, Fumiss S, Kuhlkamp V, Lacroix D, C DEC, Almendral J, Caponi D, Kuck KH et al: Catheter ablation of recurrent scar-related ventricular tachycardia using electroanatomical mapping and irrigated ablation technology: results of the prospective multicenter Euro-VT-study. J Cardiovasc Electrophysiol 2010, 21(1), pp. 47-53.
Stevenson WG, Wilber DJ, Natale A, Jackman Wm, Marchlinski FE, Talbert T, Gonzalez MD, Worley SJ, Daoud EG, Hwang C et al: Irrigated radiofrequency catheter ablation guided by electroanatomic mapping for recurrent ventricular tachycardia after myocardial infarction: the multicenter thermocool ventricular tachycardia ablation trial. Circulation 2008, 118(25), pp. 2773-2782.
Della Bella P, Baratto F, Tsiachris D, Trevisi N, Vergara P, Bisceglia C, Petracca F, Carbucicchio C, Benussi S, Maisano F, Alfieri O, Pappalardo F, Zangrillo A, Maccabelli G,. Management of Ventricular Tachycardia in the Setting of a Dedicated Unit for the

(56) References Cited

OTHER PUBLICATIONS

Treatment of Complex Ventricular Arrhythmias: Long Term Outcome after Ablation, Circulation 2013, 127(13): pp. 1359-1368.
Extended European Search Report issued Jan. 16, 2017 in corresponding EP Patent Application No. 14798103.
Kawara, et al., "Activation delay after premature stimulation in chronically diseased human myocardium relates to the architecture of interstitial fibrosis", Circulation, 2001, 104(25): 3069-75.
Lambiase, et al., "High-density substrate mapping in Brugada syndrome: combined role of conduction and repolarization heterogeneities in arrhythmogenesis", Circulation, 2009, 120(2): 106-17.
Saumarez, et al., "The Significance of Paced Electrogram Fractionation in Hypertrophic Cardiomyopathy", 1995, 91(11): 2762-8.
Stevenson, et al., "Fractionated endocardial electrograms are associated with slow conduction in humans: Evidence from pacemapping", J Am Coll Cardiol., 1989, 13(2): 369-76.

* cited by examiner

SYSTEM AND METHOD FOR DECREMENT EVOKED POTENTIAL (DEEP) MAPPING TO IDENTIFY COMPONENTS OF THE ARRYTHMOGENIC CIRCUIT IN CARDIAC ARRHYTHMIAS

CROSS-REFERENCE TO RELATED APPLICATION

This application claims the benefit of U.S. Provisional Patent Application No. 61/824,457, filed May 17, 2013; the entire contents of Patent Application No. 61/824,457 are hereby incorporated by reference.

FIELD

The various embodiments described herein generally relate to a system and method for identifying the critical components of the arrhythmogenic circuit.

BACKGROUND

Heart tachycardia is an abnormally fast rhythm of the heart caused by abnormal electrical propagation. This can be either caused by surviving strands of tissue following a cardiac infarct or a defect in the electrical conduction system of the heart. This abnormal rhythm affects the pumping function of the heart and if not treated could be life-threatening.

Therapies to control tachycardias mostly consist of the use of an implantable Cardiac Defibrillator (ICD), an anti-arrhythmic drug regimen, or ablative strategies. Though ICDs successfully terminate the Ventricular Tachycardia (VT), they do not eliminate the arrhythmogenic substrate and hence do not prevent future recurrences of VT episodes. Anti-arrhythmic drugs, on the other hand, might reduce the incidences of VT occurrences in some patients but have some significant side effects. Ablative strategies, however, reduce and or prevent VT recurrence by locating and ablating the source of the tachycardia. Catheter ablation of ischemic ventricular tachycardia (VT) can be used as a treatment to reduce the burden of VT and defibrillator shocks and can be lifesaving in the event of an arrhythmic storm [R3.1, R3.2]. In addition, recent literature suggests that when VT ablation is performed successfully, it results in a significant decrease in long-term mortality [R3.22].

To facilitate ablation, cardiac mapping can be used to identify potential sites in the heart for ablation by recording electrical signals at multiple sites in the heart. Mapping can be done by either simultaneously acquiring electrograms at various locations of the heart or using a roving electrode and in both cases using surface ECG as a time reference. Local activation time for all of the electrograms can be used to indicate the path of depolarization [R1.1]. Some conventional cardiac mapping techniques used to identify potential sites for ablation include substrate mapping, activation mapping (or isochrone mapping), and entrainment mapping.

Most conventional mapping approaches require activation mapping during tachycardia (i.e. entrainment mapping) for the mapping to identify the putative source. However, these techniques cannot be used in fast or hemodynamically unstable tachycardias or under conditions when tachycardia cannot be induced on arrival to the cath lab. Instead, a variant of mapping is typically used called pace-mapping where electrical stimulation is applied to the heart and the response is mapped to simulate the VT. This mapping can produce ECG data that appears to be like clinical VT however can be produced from a wide area and not necessarily a site that produces success. In substrate mapping during sinus rhythm, a linear lesion along and transecting the scar is used for substrate modification for prevention of VT. Recently, late potential mapping and ablating all of the late potential for scar homogenization has been used; however these lesion sets are not specific and may result in ablating blind alleys and non-critical regions.

SUMMARY OF VARIOUS EMBODIMENTS

In a broad aspect, at least one embodiment described herein provides a method for determining an arrythmogenic circuit of a heart. The method comprises: obtaining data for electrograms recorded at various locations of the heart while programmed ventricular pacing with extra stimuli; is performed; identifying a sharp near-field potential beyond a QRS complex for both a base train and extra stimuli for at least two of the recorded electrograms; obtaining decrement values for at least two different locations of the heart based on measuring a time difference of the near-field potential in response to the extra stimuli and the time difference between the near-field potential in response to the base train in the at least two recorded electrograms corresponding to the different locations of the heart; generating at least a portion of a decrement map using the decrement values; and identifying the arrhythmogenic circuit based on electrograms having significant decremental properties.

In another broad aspect, at least one embodiment described herein provides a use of the methods defined herein to determine the arrythmogenic circuit of a heart for Ventricular Tachycardia (VT), Atrial Tachycardia (AT) or fibrillation.

In another broad aspect, at least one embodiment described herein provides a use of the methods defined herein in which the heart has ischemic cardiomyopathy or dilated cardiomyopathy.

In another broad aspect, at least one embodiment described herein provides a computer readable medium comprising a plurality of instructions that are executable on a microprocessor of an apparatus for adapting the device to implement a method for determining an arrythmogenic circuit of a heart, according to the various methods defined herein.

In another broad aspect, at least one embodiment described herein provides a system for determining an arrythmogenic circuit of a heart. The system comprises an input for receiving data for electrograms recorded at various locations of the heart while programmed ventricular pacing with extra stimuli was performed; and a processing unit for controlling the system. The processing unit is configured to identify a sharp near-field potential beyond a QRS complex for both a base train and the extra stimuli for at least two of the recorded electrograms; to obtain decrement values for at least two different locations of the heart based on measuring a time difference of the near-field potential in response to the extra stimuli and the time difference between the near-field potential in response to the base train in the at least two recorded electrograms corresponding to the different locations of the heart; to generate at least a portion of a decrement map using the decrement values; and to identify the arrhythmogenic circuit based on electrograms having significant decremental properties.

In some embodiments, the system may further comprise measurement and stimulation hardware that are coupled the processing unit and configured to apply programmed ventricular pacing with extra stimuli to the various locations of the heart while recording the electrograms.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment and the drawings will now be briefly discussed.

Figure 1:
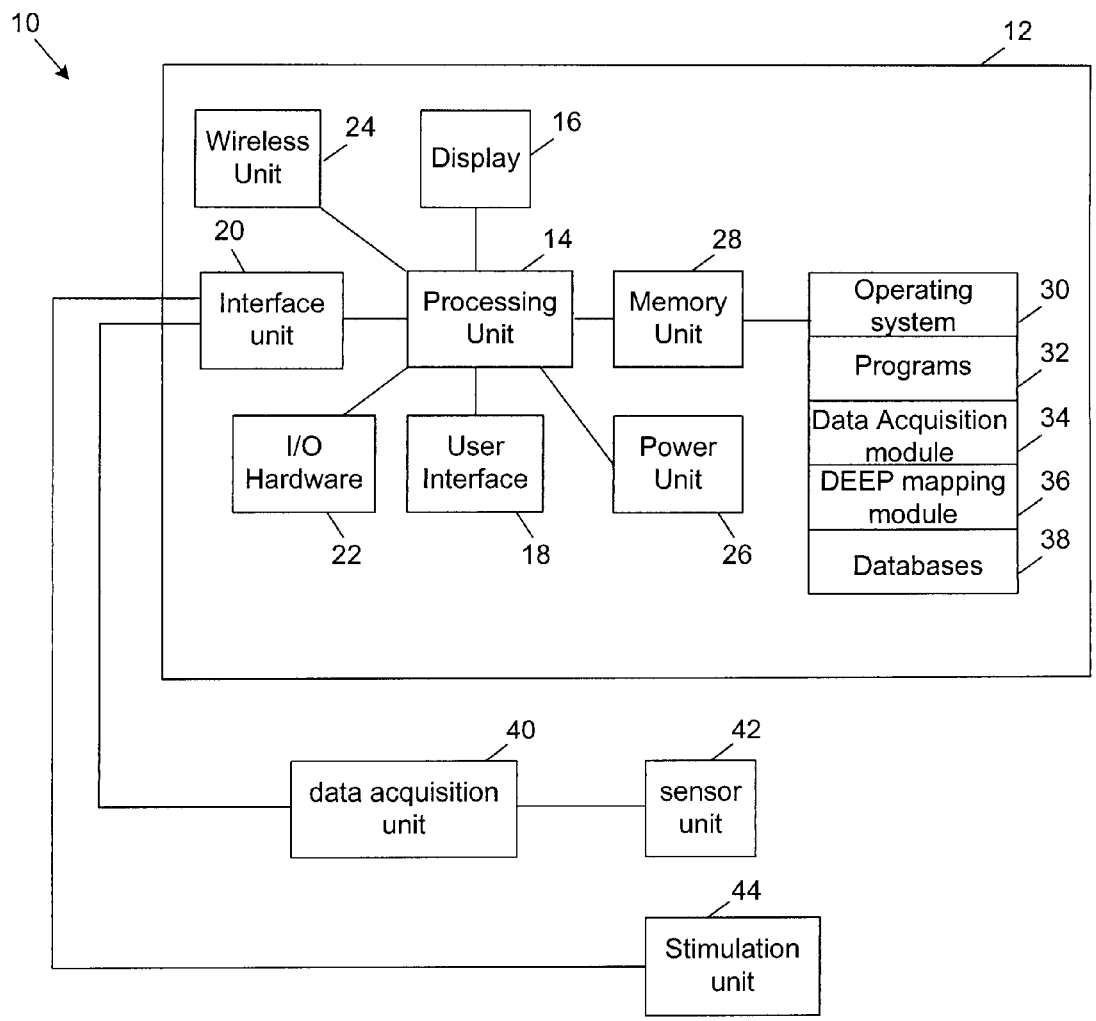
FIG. 1 is a block diagram of an example embodiment of a system that can perform Decrement EvokEd Potential (DEEP) mapping to identify critical components of the arrythmogenic circuit in cardiac arrhythmias.

Further aspects and features of the embodiments described herein will appear from the following description taken together with the accompanying drawings.

DETAILED DESCRIPTION OF THE EMBODIMENTS

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not limited to apparatuses, devices, systems or processes having all of the features of any one apparatus, devices, systems or process described below or to features common to multiple or all of the apparatuses, devices, systems or processes described below. Any subject matter disclosed in an apparatus, device, system or process described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein in any way, but rather as merely describing the implementation of various embodiments as described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate a time interval between electrical stimulation impulses. "Tight coupling" or "Closely coupled" as used herein mean a relatively short time interval between such impulses.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Activation and substrate mapping are currently utilized with significant limitation. The strategy of activation mapping during ongoing VT is limited by difficulty in inducing clinical tachycardia, the stability of the induced tachycardia, the hemodynamic stability of the patient and correctly identifying activation in the critical isthmus and blind alleys from multiple components and fractionated electrograms. Given the convenience, mapping and ablation during sinus rhythm or during pacing is often the preferred strategy in the current era of VT ablation [R3.3]. However, the targets of substrate ablations and end-points are not well defined and several different criteria of appropriate target sites and end points of ablation have been suggested [R3.7].

Optimally the ablation targets identified with substrate mapping should be all areas capable of acting as diastolic channels of the reentrant circuit in VT. However, late and pathological signals may appear in clinically irrelevant areas and targeting those areas that do not serve as substrate for reentry will lengthen the procedure with increased risk of complications.

Focused substrate based ablation can be achieved by proposing a novel target for ablation, based on the concept that electrocardiograms (EGMs) in areas that are likely to be acting as arrhythmia channels may demonstrate significant decremental properties (i.e. Decrement Evoked Potentials (DEEP) when stressed with extra stimuli having certain properties.

Described herein are various example embodiments of a system and method that can be used for identifying the arrhythmogenic circuit, which can be used for various goals including, but not limited to, VT ablation or AF treatment.

Referring now to FIG. 1, shown therein is a block diagram of an example embodiment of a DEEP cardiac mapping system 10 that can perform DEEP mapping of certain cardiac features such as the arrhythmogenic circuit. The system 10 includes an operator unit 12, a data acquisition unit 40, a sensor unit 42 and a stimulation unit 44. The system 10 further includes several power supplies (not all shown) connected to various components of the system 10 as is commonly known to those skilled in the art. In general, a user may interact with the operator unit 12 to measure ECG data from a subject or a patient and then perform DEEP mapping on the measured data to identify critical components of arrythmogenic circuit in cardiac arrhythmias. The system 10 is provided as an example and there can be other embodiments of the system 10 with different components or a different configuration of the components described herein.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, a data acquisition module 34, a DEEP mapping module 36 and one or more databases 38. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power processor depending on the configuration, purposes and requirements of the system 10 as is known by those skilled in the art. For example, the processing unit 14 may be a high performance general processor. In alternative embodiments, the processing unit 14 can include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like depending on the particular implementation of the operator unit 12.

The user interface 18 can include at least one of a mouse, a keyboard, a touch screen, a thumbwheel, a track-pad, a track-ball, a card-reader, voice recognition software and the like, again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet connection, a Local Area Network (LAN) connection, an Ethernet connection, a Firewire connection, a modem connection or a digital subscriber line connection. Various combinations of these elements can be incorporated within the interface unit 20.

The I/O hardware 22 is optional and can include, but is not limited to, at least one of a microphone, a speaker and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 is used to store an operating system 30 and programs 32 as is commonly known by those skilled in the art. For instance, the operating system 30 provides various basic operational processes during the operation of the operator unit 12. The programs 32 include various user programs so that a user can interact with the operator unit 12 to perform various functions such as, but not limited to, viewing and manipulating data as well as sending messages as the case may be.

The data acquisition module 34 may be used to obtain ECG data from a patient or subject, which may be done in response to certain stimuli. Accordingly, the data acquisition module 34 may also be used to control the timing for stimulus generation and data acquisition. This depends on whether the sensor unit 42 is a multi-electrode sensor unit or not. Portions of the data acquisition module 34 will be explained in more detail with respect to FIGS. 3 and 19.

The DEEP mapping module 36 processes the data that is acquired by the data acquisition module 34 in order to determine areas of the heart which may be important portions of the arrhythmogenic circuit. This is described in more detail with respect to FIGS. 14 to 20. This information can then be provided as an output consisting of an electronic file or a display image with information in the form of a cardiac map or another suitable form for conveying information about the arrhythmogenic circuit.

In alternative embodiments, modules 34 and 36 may be combined or may be separated into further modules. The modules 34 and 36 are typically implemented using software, but there may be instances in which they are implemented using FPGA or application specific circuitry.

The databases 38 can be used to store data for the system 10 such as system settings, parameter values, and calibration data. The databases 38 may also be used to store other information required for the operation of the programs 32 or the operating system 30 such as dynamically linked libraries and the like.

The operator unit 12 comprises at least one interface that the processing unit 14 communicates with in order to receive or send information. This interface can be the user interface 18, the interface unit 20 or the wireless unit 24. For instance, information for programming stimulation generation by the system 10 in order to perform DEEP mapping can be inputted by someone through the user interface 18 or it can be received through the interface unit 20 from another computing device. The processing unit 14 can communicate with either one of these interfaces as well as the display 16 or the I/O hardware 22 in order to output information related to DEEP mapping. In addition, users of the operator unit 12 can communicate information across a network connection to a remote system for storage and/or further analysis. This communication can also include, but is not limited to, email, text or MMS communication, for example.

A user can also use the operator unit 12 to provide information needed for system parameters that are needed for proper operation of the system 10 such as calibration information and other system operating parameters as is known by those skilled in the art. Data that is obtained from tests, as well as parameters used for operation of the system 10, may be stored in the memory unit 28. The stored data may include raw sampled data as well as processed cardiac map data.

The data acquisition unit 40 comprises hardware circuitry that is needed to record ECG data from a patient or subject in order to perform cardiac mapping. Different variations are possible for the data acquisition unit and an example embodiment is described with respect to FIG. 2.

The sensor unit 42 is used to measure the electrical information (i.e. ECG) from the heart of the patient or subject. The sensor unit 42 may only have one electrode or it may have only a few electrodes such as a single roving 4-electrode ablation catheter, for example. In other embodiments, the sensor unit 42 can be a multi-electrode sensor and may have multiple electrode arrays such as a multi-electrode endocardial electrode balloon, for example, that can be used to gather electrical information from large areas of the endocardium in a few beats. Other examples of multi-electrode sensors include, but are not limited to, basket catheters, catheters with multiple splines that allow for multi-electrode contact mapping, and non-contact mapping arrays. When these tools are used in conjunction with 3D EAM systems, these tools may provide high-density decremental maps within a reasonable time frame. The operation for different sensor units 42 in order to perform DEEP mapping is described in more detail with respect to FIG. 19.

The stimulation unit 44 is used to provide stimulus signals to the heart of the patient or subject at a certain rate set by time intervals which can range from S1 to Sx. For example, the time intervals can range from S1 to S3. The stimulation unit 44 can be a separate stimulation catheter, for example. In an alternative embodiment it may be possible to combine the stimulation unit 44 and the sensor unit 42 in a single device. For example, the stimulation unit 44 and the sensor unit 42 may be combined in a single device in the case of multi-electrode sensor arrays in which one or more of the sensors can be used to pace at one site and a different one or more of the sensors can be used to record from another site.

In alternative embodiments, the operator unit 12 can also be used in conjunction with commercially available recording systems, such as Prucka (General Electrics), Velocity (St-Jude Medical) or Carto 3 (Biosense Webster), for example. In this case, the electrograms may be exported from the recording system into the operator unit 12 for analysis.

Analog mapping systems feature real-time activation detection circuitry, and large data storage [R1.2]. They allow instant replay (in slow motion) of an activation sequence, which is an advantage in the operating room where time is a critical factor. Also, the analog activation matrix display is less sensitive to false positives and false negatives than computer generated isochronal maps [R1.3]. Since the brightness of each activation dot may be modulated proportionally to the electrogram peak negative dV/dT [R1.4], it may therefore be possible to use lower thresholds to show small potentials and to visually ignore noisy channels on the activation display. Nevertheless, these analog systems lack flexibility since the sampling rate is fixed, all channels have the same gain and typically no activation time review or editing is allowed. In addition, signal to noise ratio may be limited to analog/video recording technology [R1.2].

In contrast, digital mapping systems are more flexible and have greater analysis capabilities than analog systems. However, activation detection and generation of the activation display (or isochronal map) may usually be performed off-line. In addition, data acquisition settings (e.g. channel gain, filter, sampling rate, etc.), data processing (e.g. dV/dT and detection) and displaying of results and/or data will increase processing time directly as the number of channels increase. This overhead is challenging in the time constrained environment of a cardiac operating room.

Figure 2:
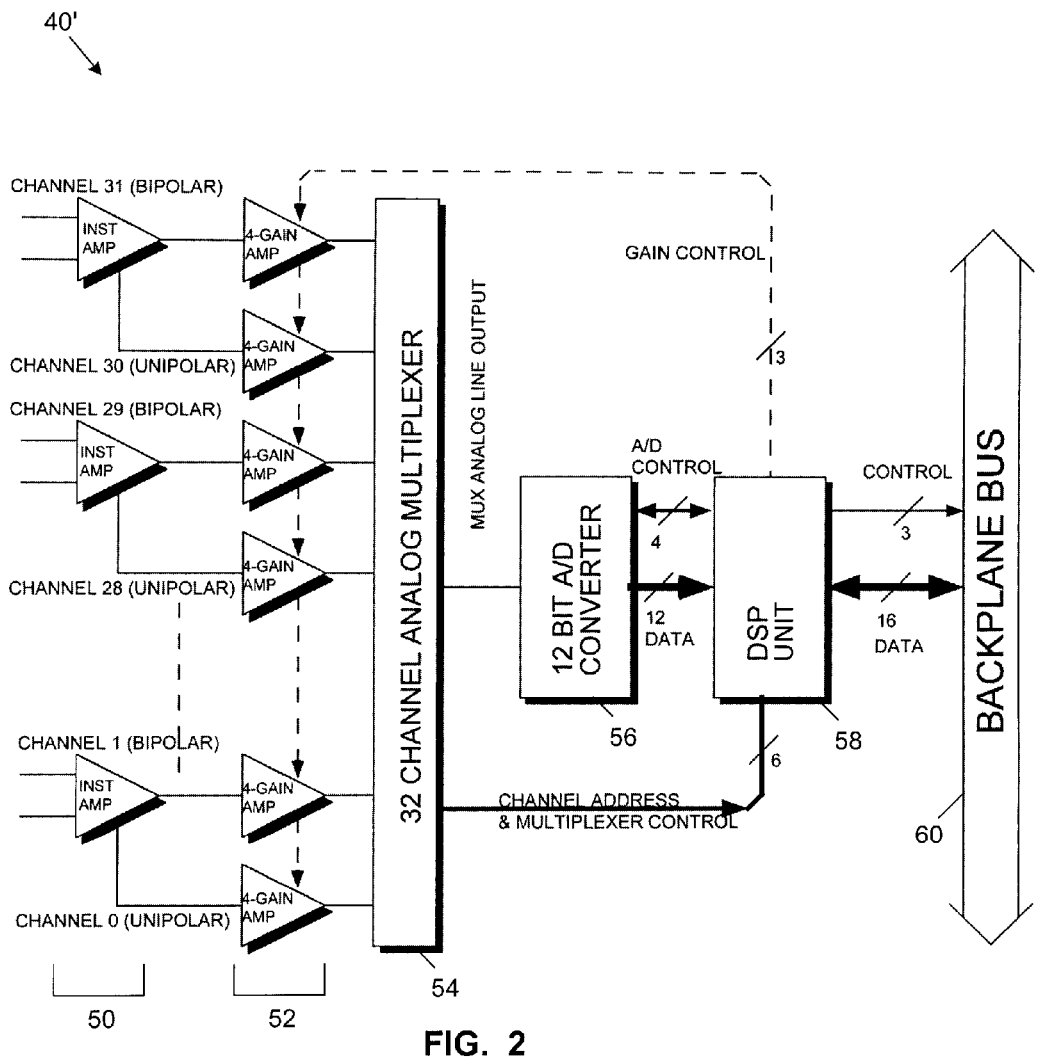
FIG. 2 is a block diagram of an example embodiment of a data acquisition unit that can be used with the system of FIG. 1.

Referring now to FIG. 2, shown therein is an example embodiment of a data acquisition unit 40' that can be used with the system 10. It should be known that other embodiments can be used for the data acquisition unit 40 as is known to those skilled in the art. In this example, the data acquisition unit 40' is a 672-channel digital data acquisition system that combines the flexibility of digital analysis with the speed of an analog cardiac mapping and may therefore be used in the operating room. Furthermore, it should be noted that while FIG. 2 refers to a custom-made mapping system; the DEEP method can be used with any other recording/mapping system.

In general, the front end of the data acquisition unit 40' comprises one controller (not shown) and 21 data acquisition boards, each having 16 unipolar and 16 bipolar channels. In FIG. 2, only one of the data acquisition boards is shown. A data acquisition board generally comprises an instrumentation amplifier bank 50 for obtaining data for the channels unipolar and bipolar channels, an amplifier bank 52, filters (not shown), a multiplexer 54, an Analog to Digital Controller (ADC) 56 and a DSP unit 58. The DSP unit 58 may be implemented by one or more processors or by specialized circuitry as is known by those skilled in the art.

In use, all channels are amplified by a corresponding amplifier in the amplifier bank 52, filtered (the filters are not shown), multiplexed by the multiplexer 54, and then digitized by the ADC 56, which in this example has 12 bits of resolution (another resolution may be used in alternative embodiments). The individual gains of the amplifiers in the amplifier bank 52 may be applied to groups of channels and may be automatically set by on-board DSP unit 58. Real-time activation detection may also be performed by the DSP unit 58 during data acquisition.

The front-end of the data acquisition unit 40' receives commands from a host computer (which may be the operator unit 12 in this example) via a communication link such as an RS-232 link, for example. Data and commands are exchanged between the acquisition boards and the controller via a common backplane bus 60.

During data acquisition, the controller reads the data from the data acquisition boards and sends the data through a fiber optic link to the host computer (in this case the operator unit 12) for storage and analysis. A multiplexer circuit may be used to interface all of the data acquisition boards to the controller. The controller may also control the data acquisition parameters (e.g. amplifier gains, filter coefficients, detection threshold and sampling sequence during data acquisition). Default sampling rates may be set to 1 KHz for unipolar and 2 KHz for bipolar channels and can be changed by modifying a sample-sequence list stored in RAM on the controller board (not shown). The front end of the data acquisition unit 40' may be battery-operated, providing full electrical isolation.

When the 16 unipolar and 16 bipolar channels are amplified, filtered, multiplexed and then digitized by the ADC 56, a total of 672 channels is provided, in this example. Since the data acquisition unit 40' is designed for a specific use, analog filters may be set at 0.5-500 Hz for unipolar channels and 23-1000 Hz for bipolar channels although other settings may be used depending on the application being performed. In addition, amplifiers may be selected so that the common mode rejection ratio on the bipolar channels is greater than about 90 dB from DC to 1000 Hz, which is more than sufficient for 12 bit resolution. Before data acquisition, the individual gain on each channel (four gain selections for unipolar: 50, 100, 200 & 400 V/V and bipolar: 1000, 2000, 4000 & 8000 V/V in this example) can be manually or automatically set by the DSP unit 58 using a serial line. The DSP unit 58 may be implemented using the TMS320 family. In some embodiments, the automatic gain setting function may be used to set the desired channels to their optimum gain setting before data acquisition, which improves time efficiency as the number of channels increases [R1.5].

During data acquisition, the DSP unit 58 may be used to detect the activation on each input data channel. For example, two different types of filters and thresholds can be defined to implement distinct detection algorithms for unipolar and bipolar signals. After detection, the DSP unit 58 may incorporate the 12 bits from the ADC 56 with 2 bits representing the channel gain and 2 bits to encode the level of activation [R1.6]. This 16-bit word may then be sent on the backplane bus 60 and subsequently read by the controller. The DSP unit 58 may also be used to control the multiplexing sequence and the interface to the backplane bus 60. In this example embodiment, the total data throughput may be 1 MSamples/s if 21 boards are used that each run at 48 KHz.

The distributed processing approach used in the data acquisition unit 40' may present several advantages such as allowing for lower throughput per DSP unit, which simplifies hardware logic design (logic speed, RAM size for the FIR filter, etc.). A low-cost DSP unit, with internal RAM and EPROM, may therefore be used to reduce both cost and board size. Also, fast, power-consuming circuits do not have to be used. Finally, expansion can be easily achieved since there are capabilities for more data acquisition boards to be added to the data acquisition unit 40'.

Figure 3:
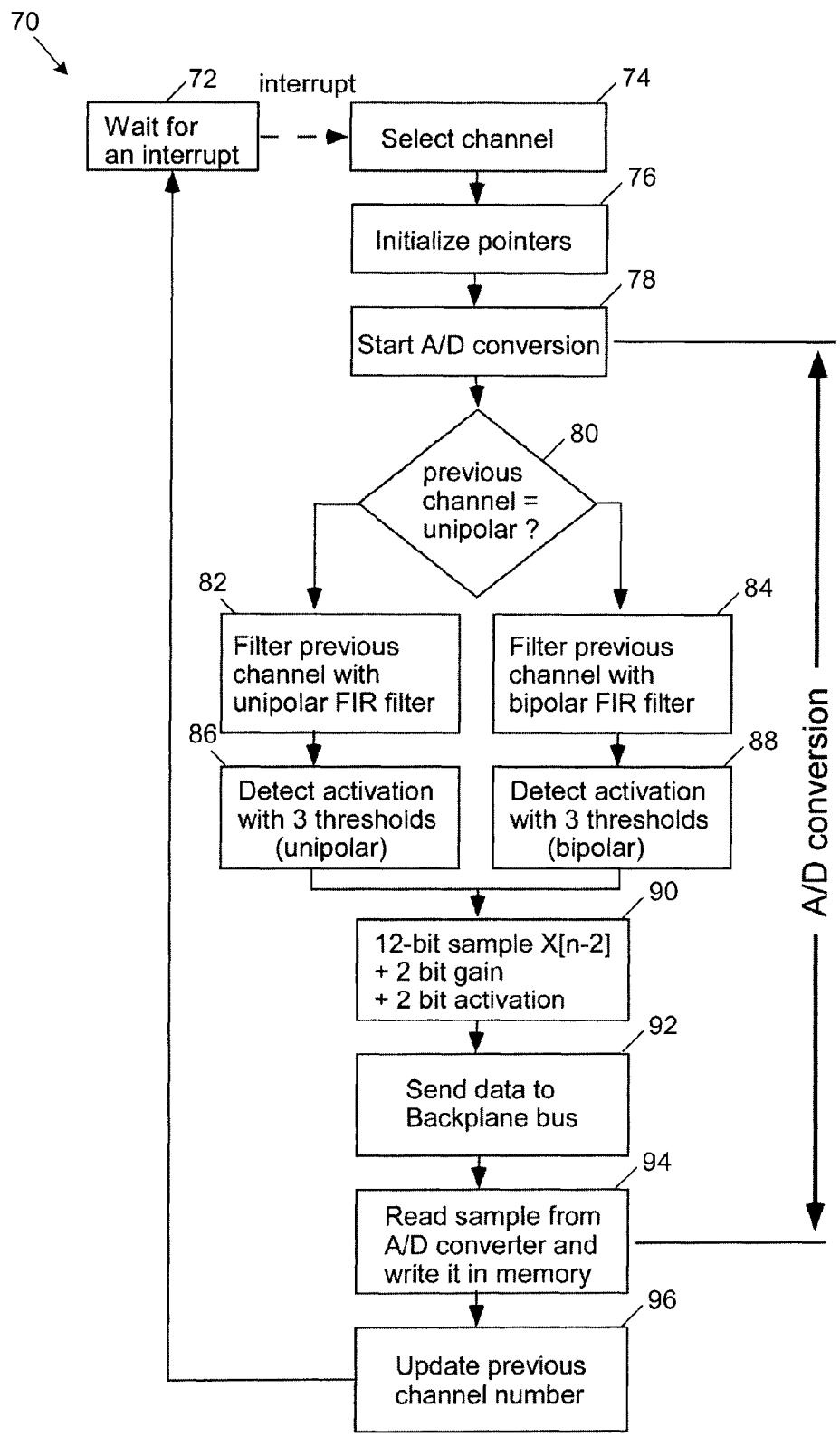
FIG. 3 is a flowchart of an example embodiment of an activation detection method that can be used in data acquisition.

Referring now to FIG. 3, shown therein is a flowchart of an example embodiment of an activation detection method 70 that may be used in data acquisition [R2.1] for the system 10 for automatic activation detection and automatic channel gain setting on each channel of the data acquisition unit 40'.

Real-time activation detection may be performed in parallel by using a plurality of local DSPs (21 in this example) along with a 5 point FIR filter and a three-threshold detector (other types of filters and detectors may be used in other implementations). The execution time may be about 20 µs, which is fast enough to process a 48 KHz multiplexed signal (e.g. 16 unipolar channels at 1 KHz sampling rate+16 bipolar channels at 2 KHz sampling rate) on each data acquisition board, giving a total throughput of about 1 MSamples/s (e.g. 21 boards at 48 KHz/board each).

The data acquisition module 34 may be divided into 3 major components: 1) a monitor section that communicates with the controller board via the backplane bus 60 to exchange system parameters such as filter coefficients, channel gain, detection thresholds, etc., 2) an activation detector, and 3) a dynamic range section that may be used to set the gain used by the amplifier bank 52 on any group of channels 50 to more effectively use the full dynamic range of the ADC 56.

As shown in FIG. 3, first, the DSP unit 58 may be interrupted at 72 by the controller for an A/D conversion. Then, at 74, the DSP unit 58 may select a particular channel requested by the controller by using the multiplexer 54. Pointer initialization (for filter coefficients and data table) may occur at 76 and take just enough time (about 2.2 µs in this example) so that the sample is stable before A/D conversion occurs at 78. During A/D conversion (about 9 µs in this example), at 82 and 84, the DSP unit 58 may filter the previous channel using a 5 point FIR (finite impulse response) filter (not shown) according to equation 1:

$$Y[n-2]=a_1X[n-4]+a_2X[n-3]+a_3X[n-2]+a_4X[n-1]+a_5X[n] \quad (1)$$

where $Y[n-2]$ is the filter output with a delay of two samples, $X[n]$ is the last sample of the previous channel and $a_n$ are user-defined coefficients. These filters can be used to implement dV/dT algorithms as are known by those skilled in the art [R2.4]. The level of the filters can be adjusted depending on the size of the RAM of the DSP unit 58.

Figure 4:
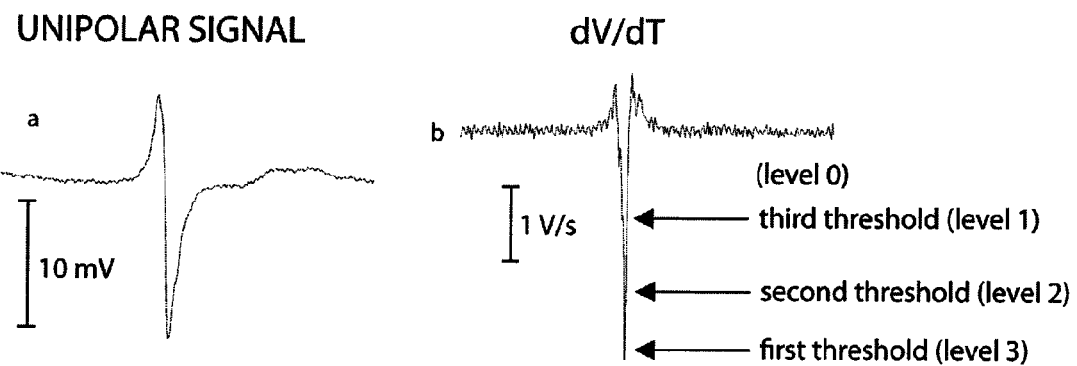
FIG. 4 is a diagram illustrating activation detection using the method shown in FIG. 3.

After filtering, activation may be detected at 86 and 88 by comparing the filtered data with three thresholds for either unipolar or bipolar data as the case may be. An example of this is shown in FIG. 4 in which the left hand panel shows a unipolar electrogram and the right hand panel shows the dV/dT of that unipolar electrogram and three thresholds. Two sets of thresholds (86 and 88) and two sets of filters (82 and 84) may be used to implement distinct algorithms for unipolar and bipolar channels.

In this example, a three-level threshold detector may be used in order to approximate the intensity-modulated analog detection found in analog cardiac mapping systems [R2.5]. On these systems the brightness of an activation dot is proportional to the peak of the negative potential derivative dV/dT. If the filtered signal goes lower than the first threshold, a flag may be set (indicating a high dV/dT). If this test fails, the same procedure is repeated for the second and the third thresholds. The thresholds can be user defined. The use of three thresholds quantifies the activation in four levels where level 0 represents no activation and level 3 represents a clear activation. The intermediate states 1 and 2 may reflect the presence of noise, artifacts or small intrinsic deflections.

After detection, at 90, the DSP unit 58 may incorporate the 12 bits from the previous channel (X[n−2]) with 2 bits for the channel gain and 2 activation bits to form a 16 bit word which is sent to the backplane bus 60 at 92 and subsequently read by the controller and written to memory at 94. This sample may be used for the next activation detection. The activation detection method 70 then updates the previous channel number at 96 and returns to a loop and waits for the next interrupt at 72. In this example, the execution time for this routine (including overhead) was about 20 μs, which is fast enough to process 16 unipolar channels sampled at 1 KHz and 16 bipolar channels sampled at 2 KHz (i.e. a 48 KHz throughput or 21 μs period).

Between recording sessions, automatic gain setting may be used to improve or optimize the A/D dynamic range of the ADC 56 on all or some of the input data channels. In this respect, the data acquisition module 34 may scan all selected channels for a given period and store minimum and maximum values for each channel in memory. This scanning period may be user defined and may be long enough to include at least two or three heart beats (the scanning period is equivalent to the time constant of a low-pass filter on an analog AGC circuit). The data acquisition module 34 may then adjust the gain on each selected channel to avoid clipping or attenuation. Once the gains are adjusted, the DSP unit 58 may then download the new gain settings to the analog amplifiers in the amplifier bank 52, which can be done using a local serial line, for example.

Study

Patients

A study was performed that included both intraoperative mapping and cathlab cases of ventricular and atrial tachycardia. The first part of the study included 6 patients with a history of remote myocardial infarction and recurrent VT. These patients were refractive to medical therapy and were scheduled for cardiac surgery and intraoperative VT ablation. The second part of the study included three patients who were scheduled for catheter ablation. Two cases were patients with previous histories of VT in the setting of prior myocardial infarction. The third case, a woman born with tricuspid atresia who had been palliated in childhood with a Fontan procedure (right atrial appendage to pulmonary artery), was scheduled for atrial tachycardia (AT) ablation.

Mapping Tools

Intra-operative mapping tools: The details of the methodology of intra-operative mapping [R3.8, R3.9] and long-term follow up [R3.10] have been described previously. Briefly, the heart was accessed via a median sternotomy and a cardiopulmonary bypass was initiated. The intraoperative mapping was performed by a custom-made 112-electrode endocardial balloon, which was inserted into the left ventricular (LV) cavity via a left atriotomy and filled with saline to ensure adequate endocardial contact. Each electrode was made of two 2 mm diameter silver beads separated by 0.1 mm from which bipolar electrograms were derived.

Cathlab mapping tools: For the catheterization laboratory cases mapping was performed with a basket catheter (Constellation, Boston Scientific) and Crista Catheter (Biosense Webster). However, it should be noted that the DEEP method described herein is mapping catheter agnostic so other types of catheters may also be used such as, but not limited to, a general EP catheter or an ablation catheter, for example.

The bipolar electrograms were amplified, filtered and recorded using the system 10, data acquisition unit 40', and the activation detection method 70 [R3.20, R3.21]. Filter settings were 28-750 Hz for bipolar electrograms. A very high amplification was selected for bipolar EGMs (about 15000-20000 V/V). A small inter-electrode distance was used for the bipolar electrodes to allow measurements of very small, local potentials in the range of 50-100 μV. High gains were chosen to reveal the small diastolic potentials and to improve the mapping process. The electrograms were digitized at 2 Ksamples/s and stored in memory for analysis.

It should be noted that this is only one example of a system that may be used to implement the method of DEEP mapping described herein as the DEEP mapping method is mapping system agnostic.

Mapping and Ablation Protocol

For VT cases (intraoperative and cathlab cases), VT was induced by right ventricular (RV) pacing the introduction of premature extra-stimuli (S2-S3) after a paced train (S1) at a basic cycle length of 400-600 ms. The clinical relevance of induced VT was confirmed by comparison of surface lead ECG acquired during clinical VT or from a prior electrophysiological study. For the sole AT case, AT was ongoing at the time of the study, but was terminated during mapping, at which time programmed stimulation was performed for the study of the DEEP technique. During stimulation, 3-dimensional anatomical shells were made using clinical mapping utilities (St Jude Nav-X Velocity and Biosense Webster Carto 3), over which electrogram-based data could be superimposed. The EGM data was stored in memory for later analysis.

Substrate Map

Two-dimensional color-coded endocardial maps were created from the bipolar EGM data acquired during the mapping procedure. Maps were displayed as "bulls-eye" plots with the apex in the middle and the basal left ventricle at the periphery. The plots were aligned so that electrode row 1 was at the line of the anterior intraventricular septum and the rows subsequently continued clockwise to the lateral, posterior and septal endocardial walls of the LV. Four types of maps were created for each patient. Scar maps, which are voltage maps, were created during Sinus Rhythm (SR), with a threshold of 0.5 mV for scar. The threshold was adjusted to give the optimal contrast of the scar border. LP maps were created during RV pacing by tagging all sharp near-field potentials occurring after the paced QRS complex.

Late Potential Mapping

Late potentials are local potentials (activations) occurring after the end of the QRS complex as seen on the surface ECG. These potentials have high frequency and variable amplitude and are reproducibly seen, with reproducible timing from repetitive paced beats. Abnormal potentials can frequently be seen within the QRS complex, which is one of the reasons, that they may not be the most sensitive target for substrate based ablations of VT. To overcome this problem, some researchers have coined the term left ventricular abnormal local activation or LAVA. However, the issue here is the obvious subjectivity of the operator and the risk that these signals are non-specific targets, hence risking excessive ablation at sites that do not have the properties to induce or sustain re-entrant ventricular tachycardia.

Accordingly, the areas of late potentials during SR and pacing in both the endocardial and epicardial surfaces were also characterized in the study. Color-coded substrate maps were created with the application of scar mapping and LP mapping during SR and RV pacing. The areas of LPs were defined as any local activity after the end of the surface QRS. Very late potentials (VLP) were defined as local activity more than 50 ms from the end of the surface QRS.

Activation Map During VT

Figure 5:
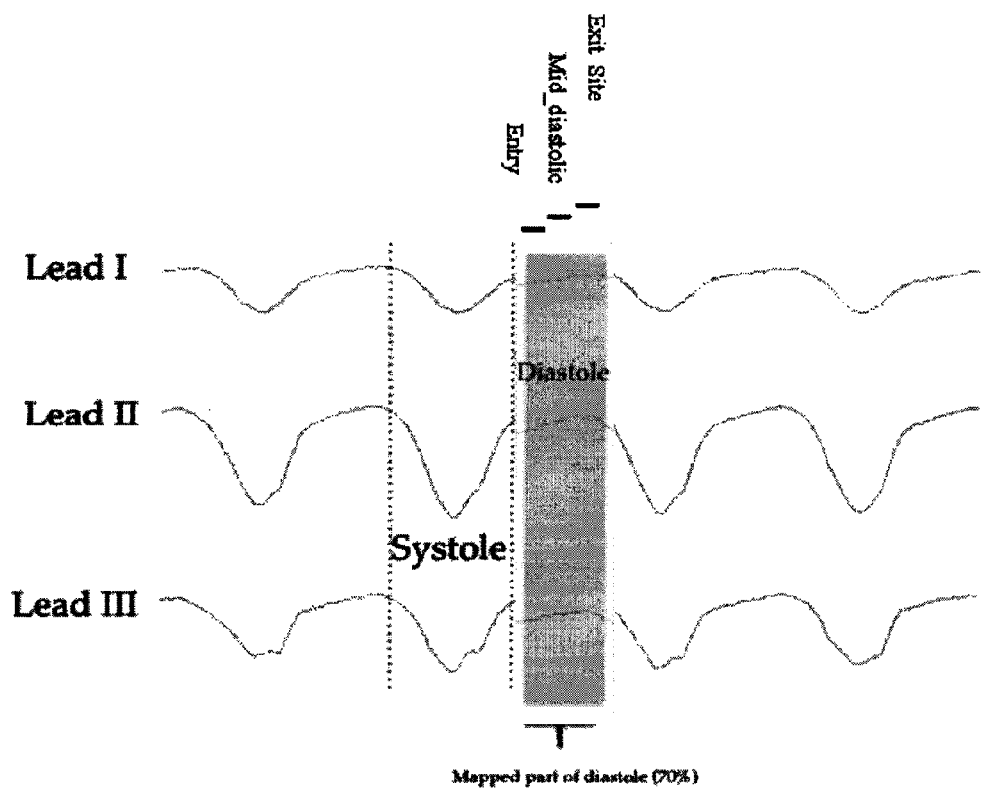
FIG. 5 is a diagram illustrating an example surface recording during Ventricular Tachycardia (VT).

The diastolic interval was defined as the time between the end of the surface QRS complex in any lead and the beginning of the next complex in any lead. After induction of VT, all areas with electrical activity during diastole were displayed, including activation in so called bystander areas. Care was taken to only annotate true near-field diastolic activity based on sharp near-field EGMs displaying a high dV/dT. The diastolic period during VT activation was then divided into 3 evenly divided portions in time, termed entry, mid-diastolic, and exit sites. This can be seen in FIG. 5 and all three of these portions have the same time duration during diastole.

Late Potential Mapping and Diastolic Activation of VT

Ablation of ischemic VT is limited by the fact that only a subset of patients can be mapped and ablated during tachycardia. Substrate mapping aims to define the arrhythmogenic substrate and identify potential channels. The aim of this study was to examine the efficacy of late potential (LP) substrate mapping in defining the critical components of the diastolic pathway during VT. This was done by analyzing detailed LP maps during pacing and comparing these LP maps to diastolic activation maps during VT. The diastole was carefully mapped and diastolic activity sites were marked as entry, mid-diastolic and exit sites. Bystander sites were defined as areas on activation mapping with no adjacent activation.

Decrement Evoked Potential Mapping

Figure 21:
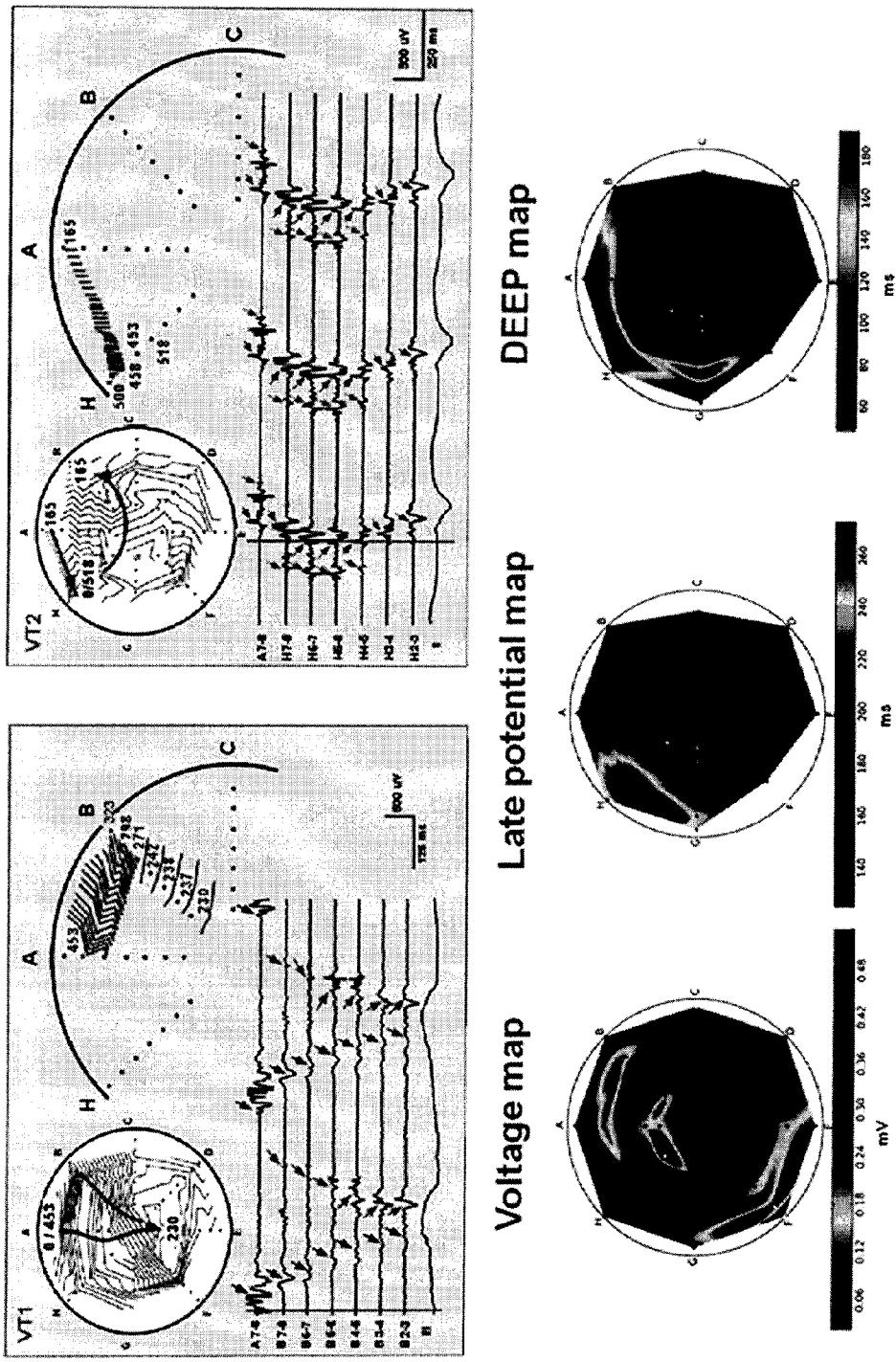
FIG. 21 is a diagram illustrating an example of DEEP mapping in the clinical setting of post-infarction ventricular tachycardia ablation.

The basis of this mapping technique is to identify the decrement in isolated near field potentials during extrastimuli. Similar to substrate mapping, during programmed ventricular stimulation with two to three extra stimuli (S2 and S3), the latest sharp near-field component of the bipolar signals during the base train and extra-beats was carefully annotated and displayed on activation time maps. The difference in timing of the isolated potentials during the base train and extra-stimuli, and the successive differences denote the decrement of activation in these potentials (for example from about 10 ms up to about 180 ms as seen in FIG. 21). Due to global decrement in the surface ECG signals, the local activation time was corrected to the global decrement in order to selectively display areas with more decrement than that seen in the global surface QRS complex (see FIG. 6 for example). All significant decrements (e.g. decrements >10 ms over the global decrement) were displayed on the maps.

In other words, during the delivery of extra-beats, it was observed that with shorter coupling intervals there was a progressive decrement in conduction velocity of the myocardial tissue (global decrement). This was corrected for by subtracting the global decrement from the decrement seen in the areas related to a scar. The 10 ms cut-off was arbitrarily chosen at the onset in order to focus the attention to the areas of greatest decrement. These cut-off windows may be manually set for each patient.

Figure 6:
FIG. 6 is a diagram illustrating two bipoles located near a VT exit site of a heart.

Referring now to FIG. 6, shown therein are two bipoles located near a VT exit site of a heart. Surface ECG is shown for reference. The RV pacing artifact is annotated with dotted lines. Following the pacing spike, a low frequency far field ventricular electrocardiogram (EGM) is seen followed by a high frequency near field EGM. In bipole 1, the near field EGM does not show significant decrement, whereas in bipole 2 the near field signal clearly demonstrates progressive decrement until it blocks (indicated by * in FIG. 6). This suggests anisotropic conduction in this area with the formation of a unidirectional block at the exit site.

Relating DEEP Mapping to Diastolic Activation During VT

The diastolic period during VT was annotated and divided into 3 evenly sized portions, termed entry, mid-diastolic and exit sites. The bipoles that demonstrated activation during diastole were then compared to the bipoles demonstrating DEEP and LP respectively. Also the bipoles showing LP were correlated to DEEP and vice versa. Values were presented as mean±SD, except the percentage of sites containing LPs and DEEPs respectively were given as percentages. A one-sample t-test was used for comparison between the overlap of signals respective to diastolic map sites. A probability value <0.05 was considered statistically significant.

Results

Substrate Mapping

All patients demonstrated areas of LP and DEEP, with an area of 21±6% and 18±4% respectively, p=ns. There was overlap in areas demonstrating both LP and DEEP of 7±2% of the endocardial surface. Areas with LP also demonstrated DEEP in 37±13% of electrode pairs, and vice versa DEEP areas similarly demonstrated LPs in 45±19%. The sensitivity of the substrate mapping in terms of identifying areas of diastolic activation was significantly higher for DEEP (50±23%) than for LP mapping (36±32%, p<0.05). Similarly, the specificity of DEEP mapping (43±23%) was significantly higher than the LP mapping (20±8%, p<0.01). DEEP mapping identified all nine VT exit sites, whereas LP mapping identified 5/9 exit sites. In addition, DEEP mapping identified more areas of mid-diastolic activity compared to LP mapping (7/9 vs. 5/9).

Activation Mapping of VT Diastole

During the first phase of the study, six patients and 9 VTs (3 patients with 2 VTs each) were analyzed. Four of the patients had previous anterior infarction and two had inferior infarctions. The areas of slow conduction during VT displayed second degree block, both 2:1 (see FIG. 7) and decremental Wenckebach periodicity (see FIG. 8). The areas displaying diastolic activity were found within areas of scar or scar borders in all patients. An example of a voltage map and an associated diastolic pathway is seen in FIG. 9. In all mapped VTs, at least ⅔ of the diastolic pathway was mapped (see FIG. 10). The area encompassed by diastolic activation was on average 18.8±9.7% of the total endocardial surface area. Similarly the LPs and decremental potentials during programmed stimulation were annotated after delineation of the VT circuit (see FIG. 11). During the extrasystoles, a reversal of activity was evident in addition to a shift in the activation pattern, indicative of unidirectional block and activation from the opposite direction (see FIG. 12). In FIG. 13, an example of the different maps resulting from different methods is demonstrated.

Figure 7:
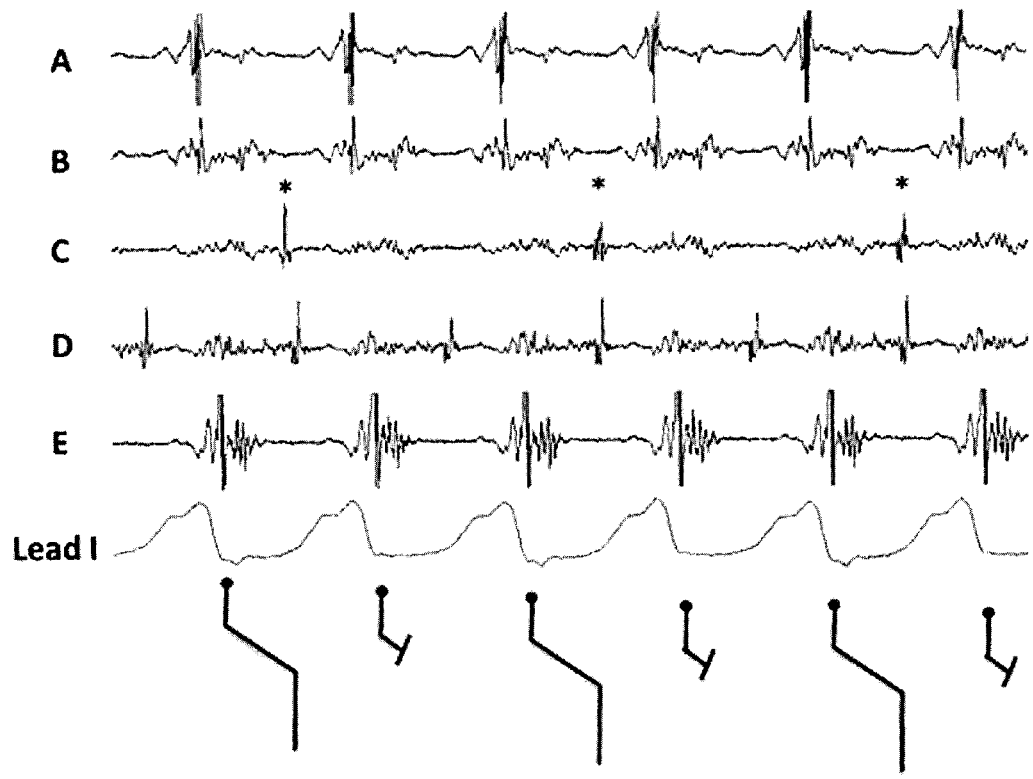
FIG. 7 is a diagram illustrating a multi-electrode recording showing five adjacent bipoles in one electrode row during VT.

Referring now to FIG. 7, shown therein is a multi-electrode recording showing five adjacent bipoles in one electrode row during VT. Surface lead I is depicted for reference. In electrodes A and B, a fractionated potential is clearly seen where the ventricular far-field is seen during systole and the near-field complex electrocardiogram is located in early diastole. The asterisk marks a signal that, on the first beat seems late in diastole, but clearly shows evidence of 2:1 conduction and is a typical bystander region.

Figure 8:
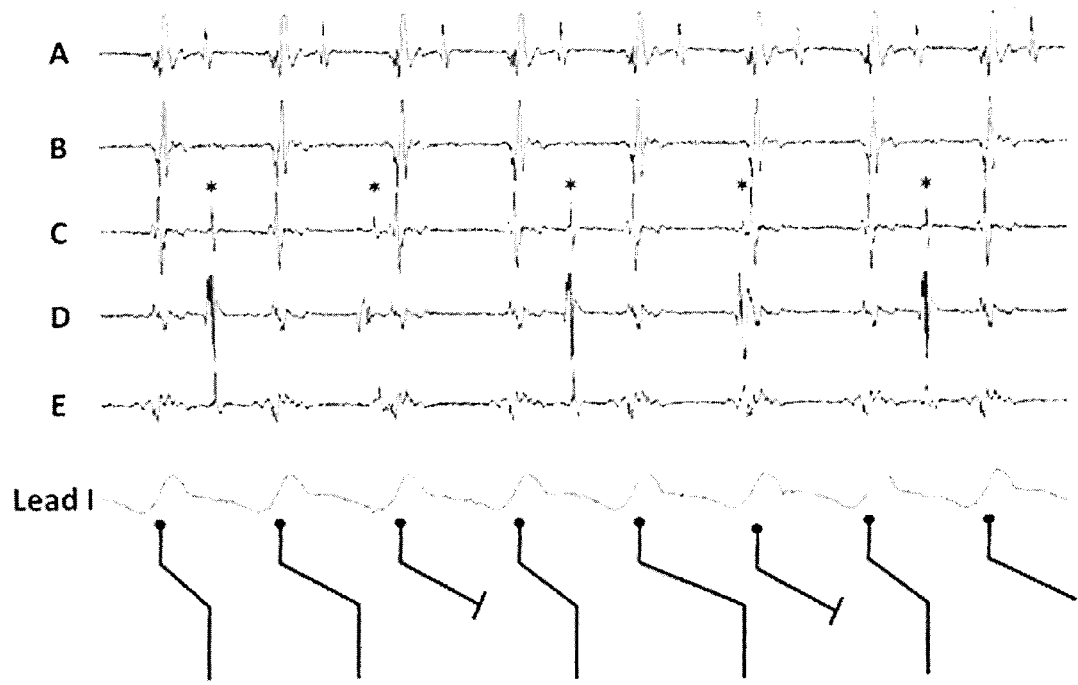
FIG. 8 is a diagram illustrating a multi-electrode recording showing six adjacent bipoles in one electrode row during VT.
Figure 9:
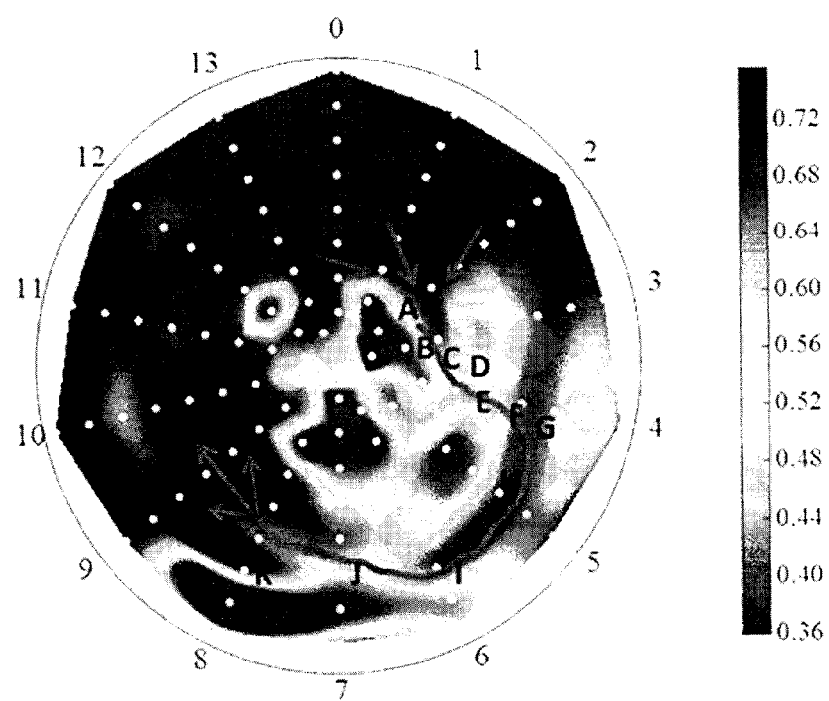
FIG. 9 is a diagram illustrating a bull's eye plot of the Left Ventricle (LV).

Referring now to FIG. 8, shown therein is a multi-electrode recording showing six adjacent bipoles in one electrode row during VT. Surface lead I is depicted for reference. In electrode A, a split potential is clearly seen where the ventricular far-field is seen during systole and the near-field electrocardiogram (second component) is located in early diastole. The asterisk marks a signal that on the first beat seems mid-diastolic, but clearly shows evidence of decremental conduction in a Wenchebach-like pattern. This signal is clearly seen on adjacent bipoles C-E.

Referring now to FIG. 9, shown therein is a bull's eye plot of the Left Ventricle (LV). Electrode row 0 is sitting at the inter-ventricular groove at the corresponding endocardial location and the rows continue in a clockwise fashion toward the lateral, inferior and septal walls. This map depicts endocardial voltage with the corresponding color bar on the right. A heterogeneous scar is found on the apico-inferior LV that extends to the basal regions. The proposed diastolic pathway has been drawn and electrodes A through K correspond to the electrical signals seen in FIGS. 8 through 10.

Figure 10:
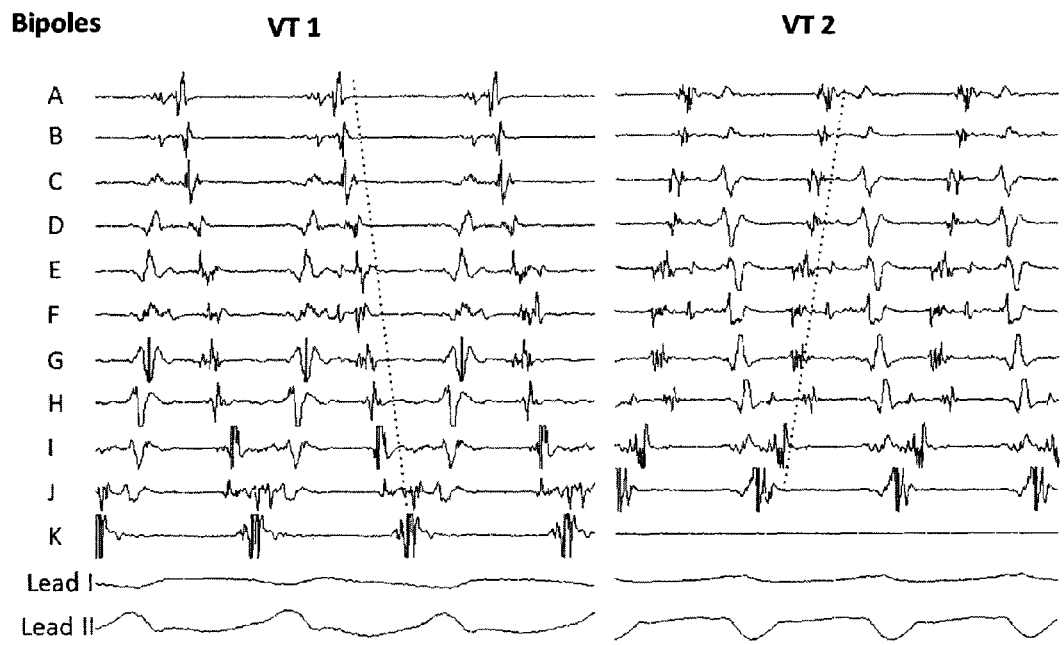
FIG. 10 is a diagram illustrating a multi-electrode recording showing eleven adjacent bipoles during VT.

Referring now to FIG. 10, shown therein is a multi-electrode recording showing eleven adjacent bipoles during VT. The corresponding anatomical location of the signals can be seen on FIG. 7. Surface lead I and II are shown for reference. On the left hand side there is a VT with an inferior axis with diastolic activation running from bipole A (entry) through mid-diastole (E-G) and finally exiting close to bipole K. After attempted pace termination a second VT was induced (on the right hand side) with an opposite activation pattern during VT and the axis was now more superior. Note the opposite wave-front on the ventricular far-field signals.

Figure 11:
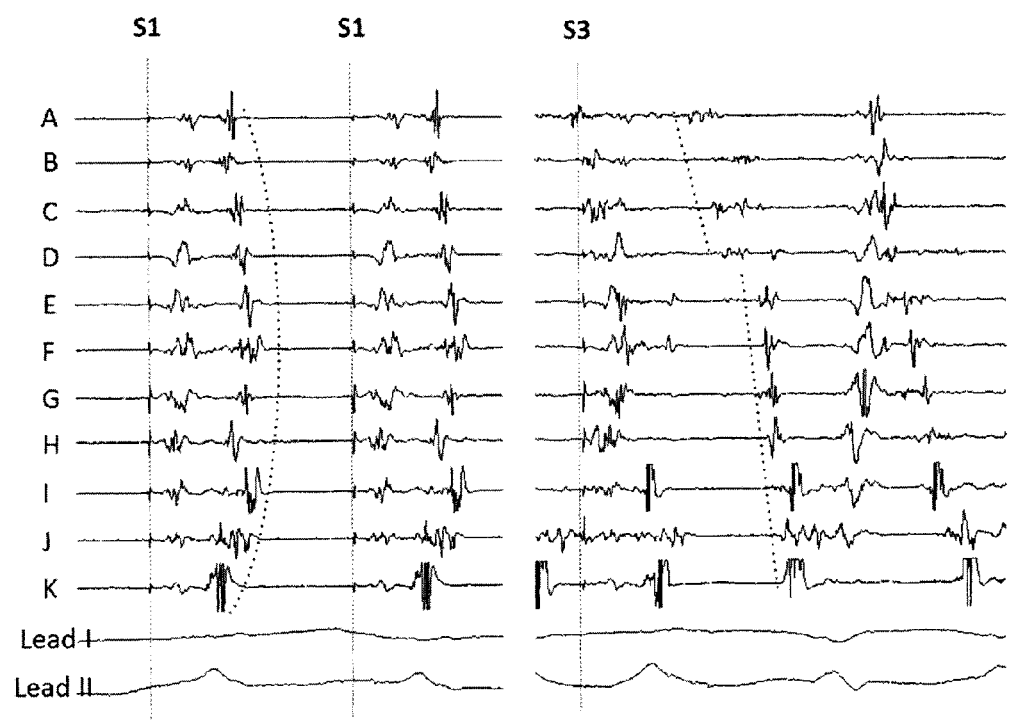
FIG. 11 is a diagram illustrating a multi-electrode recording showing eleven adjacent bipoles during right ventricular pacing.

Referring now to FIG. 11, shown therein is a multi-electrode recording showing eleven adjacent bipoles during right ventricular pacing. The corresponding anatomical location of the signals can be seen on FIG. 9 and the corresponding signals during VT in FIG. 8. Surface leads I and II are shown for reference. On the left hand side there is baseline pacing (S1-S1=600 ms) with early activation of the LV far-field and split potentials with a left concave pattern with the latest activation occurring at the middle portion of the mapped circuit. On the right hand side it is seen the last extrasystole during programmed stimulation (S3) with an activation pattern is earliest in the A bipole and then progressively later for the other dipoles. The pattern is similar to the one seen in the first induced tachycardia which is actually induced after the second beat. In bipole K, the LP is actually captured without decrement and then subsequently orthodromically activated.

Figure 12:
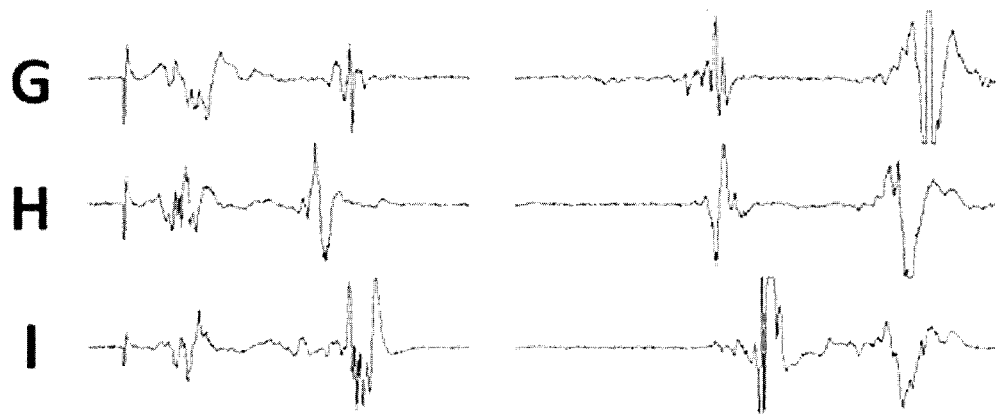
FIG. 12 is a diagram illustrating several bipoles labeled G-I with S1 pacing on the left and the last extra-stimuli on the right.
Figure 13:
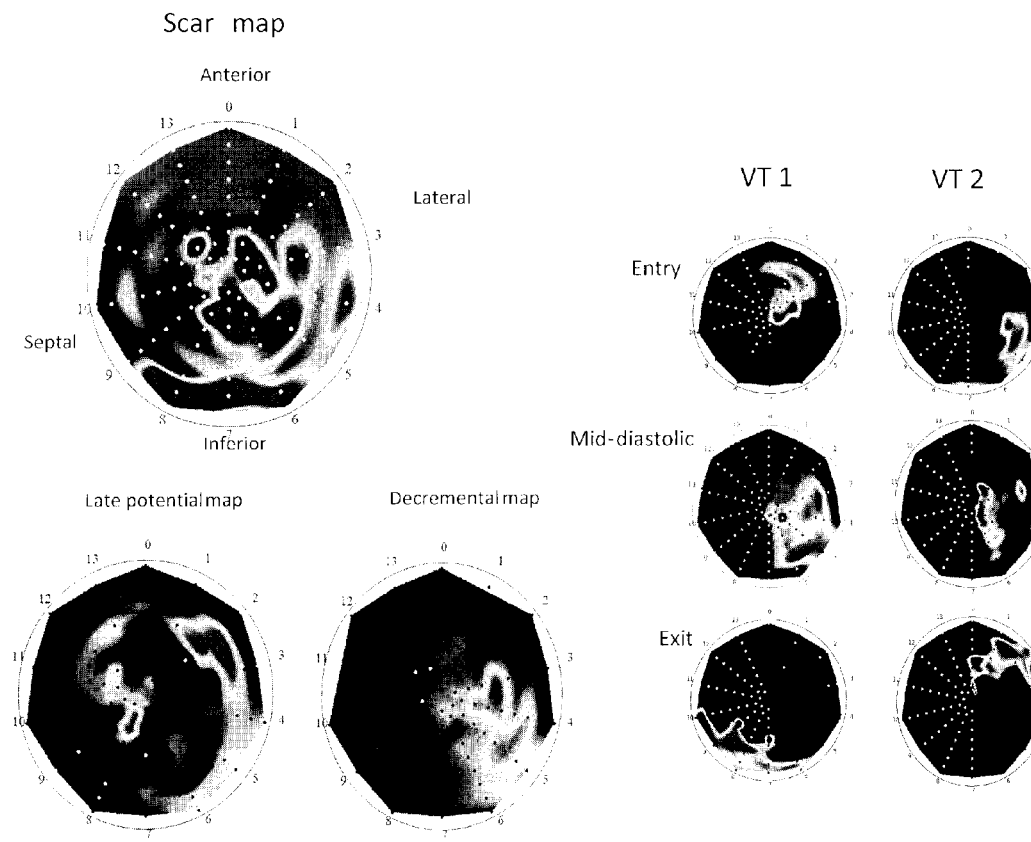
FIG. 13 is a diagram illustrating several bull's eye plots including a scar map, a late potential map, a decremental map, and the late potential maps during first and second VTs corresponding to the entry, mid-diastolic and exit regions, respectively.

Referring now to FIG. 12, shown therein are several bipoles labeled G-I with S1 pacing on the left and the last extra-stimuli on the right. A change in the activation sequence is clearly shown as well as a reversal of polarity (especially evident in bipole H), which is indicative of unidirectional block and orthodromic clockwise capture of the diastolic pathway (FIG. 7).

Referring now to FIG. 13, shown therein are several bull's eye plots including a scar map, a late potential map, a decremental map, the late potential maps during first and second VTs corresponding to the entry, mid-diastolic and exit regions, respectively. The scar map is the same as that shown in FIG. 7. On the right hand panel the two induced VTs are shown with annotation of the activation at thirds of the diastole (e.g. entry, mid-diastole and exit). The late potential (LP) map shows late activation (red) at the basal anterolateral wall and close to the septal part of the apex. During $VT_1$, the LPs correspond to the entry and for $VT_2$, the LPs correspond to the exit. The apical LP is not playing a role in either of the VTs. On the contrary, the decremental mapping is showing the most decrement at the inferolateral mid to basal wall which corresponds to the mid-diastole for both VTs.

Late Potential Mapping and Diastolic Activation of VT

A total of 16 monomorphic VTs were mapped. All of the mapped VTs were related to areas of bipolar scar. LP maps identified LPs in 25% of exit sites, 13% of entry sites and 19% of mid-diastolic sites. LPs identified critical components of the VT circuit in 56% of patients whereas 69% of LP sites were suggestive of bystander site activation during VT.

Substrate-based mapping techniques based on identification of LPs fail to identify critical areas of the VT circuit in almost half of the mapped VTs. Most LP sites represent bystander sites that are inappropriate targets for ablation.

Decrement Evoked Potential Mapping and Diastolic Activation of VT

All patients demonstrated areas of LPs and DEEPs, with an area of LPs of about 39±26%. During VT, there was activation of the endocardium in 14±7%, 12±8% and 24±11% during the entry, mid-diastolic and exit periods of the diastole. There was overlap between areas of LPs and entry sites (12±8%), mid-diastolic (11±8%) and exit sites (17±9%) but the majority of DEEP sites did not display LPs during RV pacing. At both entry and exit sites, LPs were demonstrated in 33% of patients and DEEPs in 71%. However, mid-diastolic sites demonstrated decrement in all patients, whereas the mid-diastolic sites had LPs in only 44% of VTs. LP and decrement sites that were not related to any VT were considered non-relevant sites and were not seen in any patients with decremental mapping but seen at some extent in 66% of patients when considering LPs.

Cathlab Results

VT mapping: Two different VTs were induced in the first VT case. Scar mapping demonstrated a patchy scar at the base of the basket catheter. VT mapping demonstrated by isochronal maps showed that the diastolic pathways were confined to the region marked on the scar map. Mapping of late potentials highlighted an area between electrode splines G and H of the basket catheter (see FIG. 21). Simultaneously acquired DEEP maps however demonstrated the greatest decrement in the area adjacent to splines H and A (see FIG. 21). The DEEP maps corresponded better to the postulated VT return paths, which were subsequently ablated with no tachycardia being inducible at the end of the study.

Figure 22:
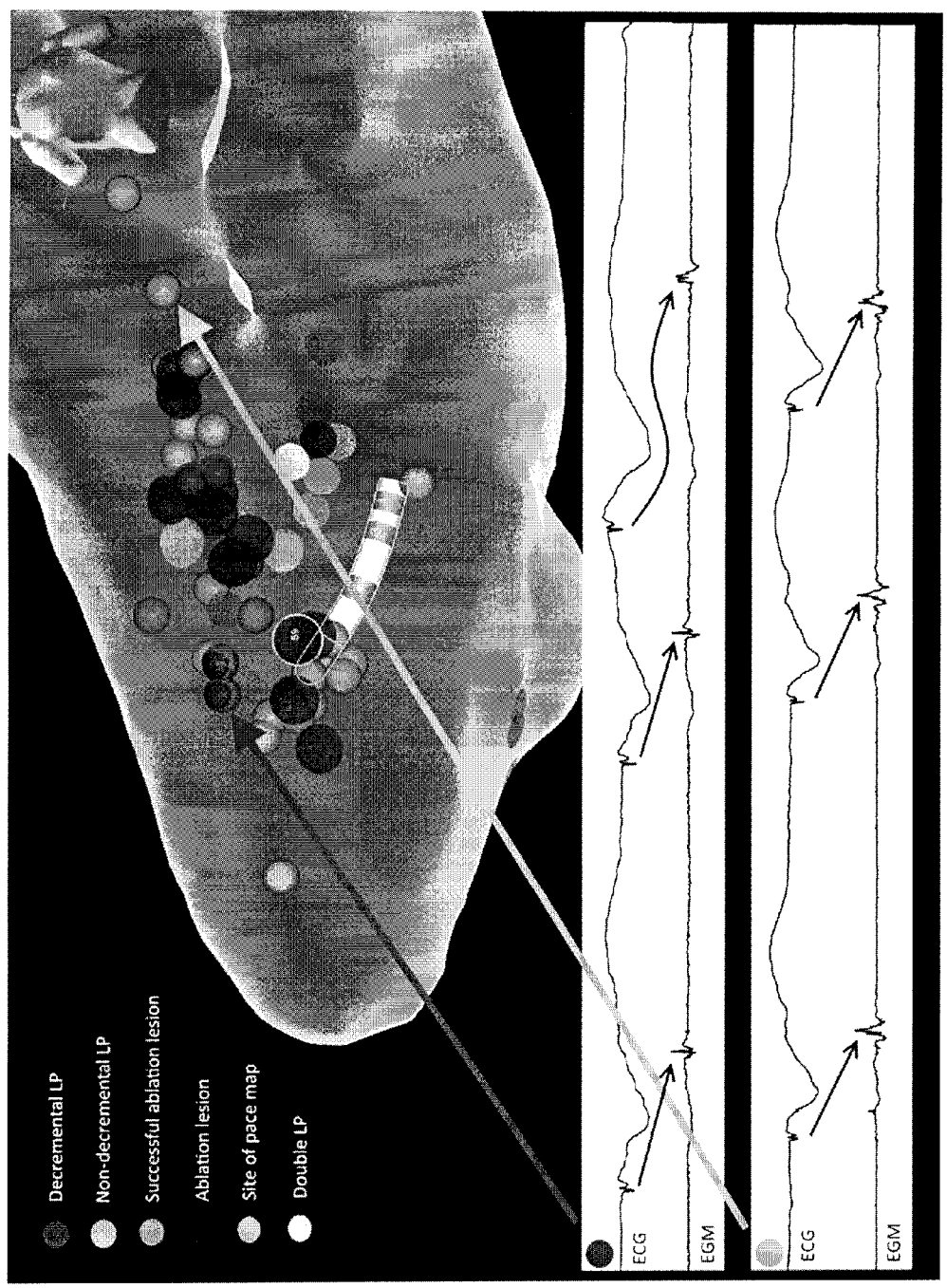
FIG. 22 is a diagram of an example of a 3D electroanatomical map in the clinical setting of post-infarction ventricular tachycardia ablation.

For the second VT ablation case, VT was induced in the Cathlab and mapped using a clinical mapping utility (St. Jude Nav-X Velocity). FIG. 22 shows the 3D electroanatomical map in the clinical setting of post-infarction ventricular tachycardia ablation in which the left ventricle is viewed from a postero-lateral view. FIG. 22 demonstrates DEEP sites (e.g. sites identified by using DEEP mapping) and their proximity to the site of successful termination of VT during radiofrequency ablation.

Figure 23:
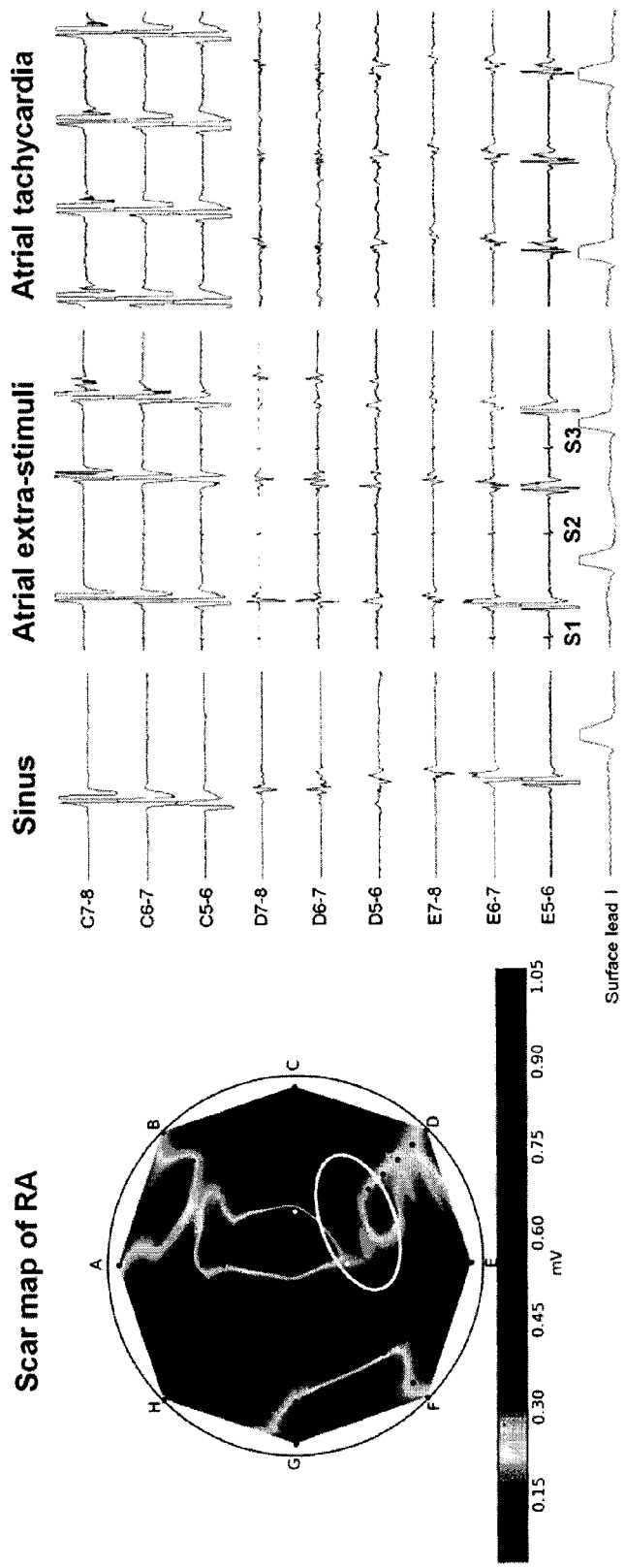
FIG. 23 is a diagram illustrating an example of DEEP mapping in the clinical setting of scar-related macro-reentrant atrial tachycardia ablation.

Atrial tachycardia mapping: The third case included an AT ablation case. The multi-electrode mapping suggested the atrial tachycardia was an intra-atrial reentry tachycardia with the critical isthmus (i.e. mid-diastolic fractionated potentials) located in the area surrounding the middle part of spline D. During catheter manipulation the tachycardia broke. DEEP mapping identified the same area (see FIG. 23). Ablation in this area rendered the tachycardia non-inducible. The voltage map suggests a patchy scar in the right atrial free wall. In the area highlighted on the voltage map, a suspected channel with diastolic fragmented signals can be seen (i.e. bipoles D5-6 through D7-8). During sinus rhythm and pacing, no clear late potentials can be seen. With the programmed extra-stimuli S2 and S3 there is obvious decrement in the potentials measured using the same electrodes which demonstrate diastolic activation during tachycardia, whereas no decrement is seen outside the channel. This suggests that this area is prone to unidirectional block and ensuing tachycardia.

Discussion

The main findings are that identifying areas of decremental properties within the scar or at the scar border can define areas which demonstrate slow diastolic activity during tachycardia, especially mid-diastolic activity, with high accuracy. The DEEP mapping was also found to be more specific than standard mapping of late potentials. These facts together suggest that the DEEP mapping methodology described herein may allow a cardiologist to deliver RF therapy with greater specificity to regions that are critical for maintaining VT.

The last decade has seen dramatic increases in patients receiving ICD implantation for the primary and secondary prevention of sudden cardiac death, although large differences between countries and regions are observed [R3.11]. Accordingly, the numbers of patients receiving appropriate therapy have also increased, as has the survival of patients with advanced cardiac disease [R3.12]. These factors have increased the number of patients being referred for VT ablations.

The main strategies for VT ablations are activation and substrate mapping. The classical method involves activation mapping and ablation during ongoing tachycardia. This allows for characterization of the diastolic pathway as various entrainment, morphological and timing criteria can then be utilized in order to separate bystander sites from the diastolic return pathway [R3.13, R3.14]. With activation mapping, important parts of the diastolic pathway can be elucidated; however in only a minority of patients is the full diastolic pathway elucidated [R3.15]. Other important drawbacks include lack of capture during entrainment, termination of tachycardia or conversion to a different tachycardia during entrainment. This strategy of activation mapping is also limited to patients who are inducible in clinical tachycardia and can endure ongoing tachycardia as mapping often involves prolonged periods of time.

Due to the limitations of activation mapping, many operators prefer the alternative method of substrate mapping which involves careful delineation of the scar and surrounding areas [R3.16]. This is usually done by carefully tagging areas having pathological potentials. Some elements of tachycardia induction and pace mapping are commonly performed in order to identify tachycardia exit sites. Substrate mapping is most commonly performed with the aid of an electro-anatomic mapping (EAM) system in order to delineate the anatomical borders of the scar area and to be able to navigate back to interesting areas for ablation. However, important drawbacks of substrate mapping include long procedure times and differing criteria on what constitutes a good target for ablation [R3.3 to R3.7]. This may cause areas to be ablated that do not have the potential to sustain tachycardia circuits and in addition areas harboring such potentials may be missed. This may in fact account for the relatively high rate of recurrence, close to 50%, seen with current ablation strategies [R3.17 to R3.19].

In support of expanding the lesion set to areas that have pathological potentials even though the areas are not found to sustain VT during the initial ablation procedure, Yokokawa et al., found that during redo ablations for VT, 47% of induced VTs were arising from areas not targeted during the first procedure [R3.6]. Another complex issue is the 20% or more of patients that have no inducible clinical tachycardia [R3.5, R3.6]. In those patients, some kind of substrate mapping is then the only real alternative, targeting LPs or local abnormal ventricular activation (LAVAs).

It should be noted that LP mapping fails to identify the critical component of the arrythmogenic circuit because it lacks the specificity needed to identify critical components of the circuit in ventricular tachycardia mapping. In the above-discussed study, of all VTs, the combined activation and LP maps identified LPs in 25% of exit sites, 13% of entry sites and 19% of mid-diastolic sites. Furthermore, of all the LP sites, 69% were suggestive of bystander sites during VT. Accordingly, it can be seen that the substrate based mapping techniques based on identification of LPs fail to identify critical areas of the VT circuit in almost half of the mapped VT's and that most LP areas represent bystander sites.

Mapping the Re-entry Circuit Using the DEEP Mapping Method

Figure 14:
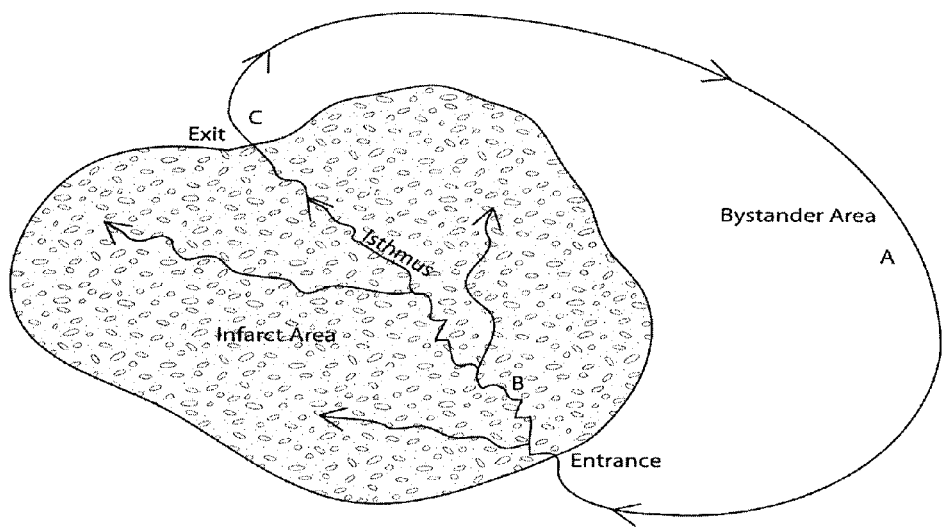
FIG. 14 is an example diagram of a heart showing reentry during tachycardia.

The majority of heart tachycardias are maintained by re-entry circuits and the purpose of cardiac mapping is to identify these circuits. These circuits are often defective parts of the heart that survived an infarct. There are two conditions for a re-entry circuit to be formed: a) the electrical wave needs to slow down and b) a unidirectional block needs to be present. The physical area where this slow conduction occurs in the circuit is called the isthmus. The objective of any mapping approach is to locate and ablate the isthmus exit point (e.g. the location where the electrical wave leaves the isthmus and starts a new wave that will excite the whole heart again). FIG. 14 shows an example of re-entry during tachycardia. Determining the isthmus exit point with precision is desirable because it shortens the ablation time, reduces the duration of the whole procedure and improves the clinical outcome. However, conventional techniques identify this area by inducing tachycardia and mapping during the tachycardia. The DEEP mapping method described herein does not require the induction of tachycardia.

Description of an Example Embodiment of DEEP

Figure 15:
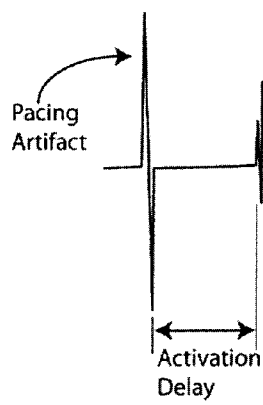
FIG. 15 is a diagram of an example response to pacing in a bystander area.
Figure 16:
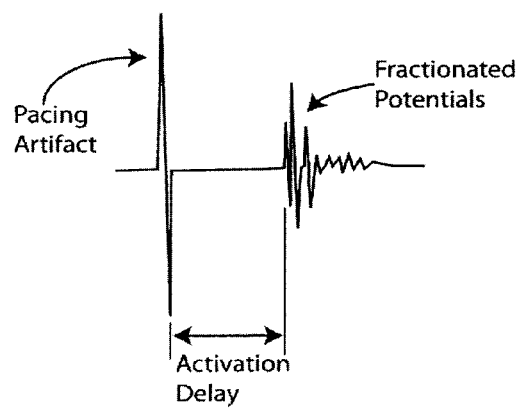
FIG. 16 is a diagram of an example response to pacing near and in the isthmus.

In one example embodiment, a roving diagnostic catheter was used during programmed stimulation with an S1-S2 protocol in which the heart is stimulated at a rate set by a time interval S1 and a premature beat after a smaller interval S2 using a separate stimulating catheter. This measurement is repeated at various sites and multiple premature beats can be generated using S3-Sx stimulation. For each location and protocol, the local heart response is measured. In a bystander area, the response to pacing results in large, short duration potentials that appear after a delay as shown in FIG. 15. Near and in the isthmus, the observed electrograms are prolonged and fractionated, (i.e. late potentials) confirming that the area is made of abnormal, slowing conductive tissue as shown in FIG. 16, for example.

Figure 17:
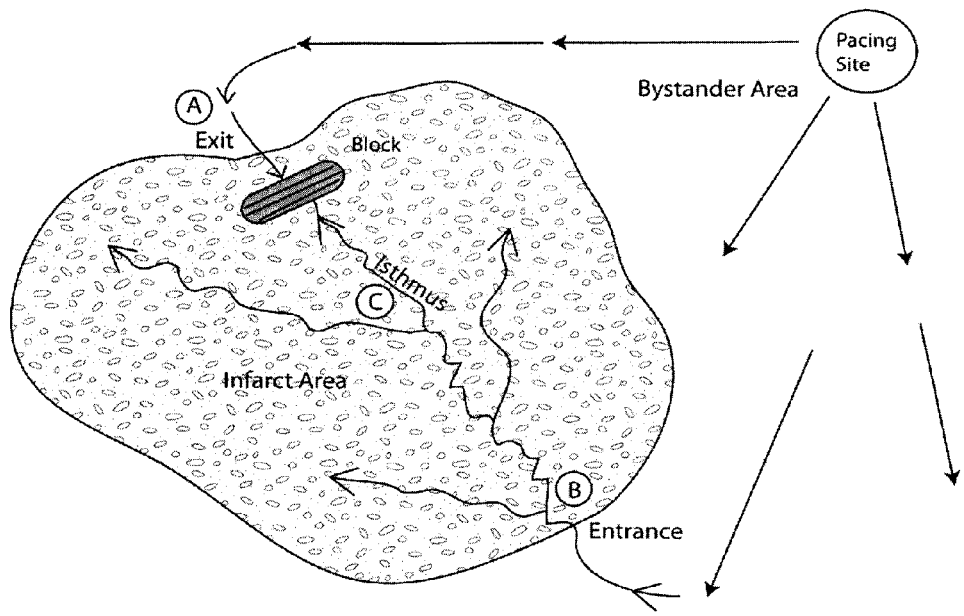
FIG. 17 is a diagram of a heart to illustrate that activation delay varies depending on the distance between the pacing and recording electrodes.

The activation delay will vary depending on the distance between the pacing electrode (i.e. stimulating electrode) and the recording electrode(s), however the fractionated potentials will dissociate as Sx gets smaller when the electrogram is recorded near the entry point of the isthmus and further decrement as the recording electrode is moved inside the isthmus. This effect is due to slow conduction, which decrements the conduction through zigzag pathways. The location where this decrement is most pronounced is at the proximity of a conduction block. At this point, the activation waves have to travel the longest distance through the isthmus. This concept is shown in FIG. 17.

Figure 18:
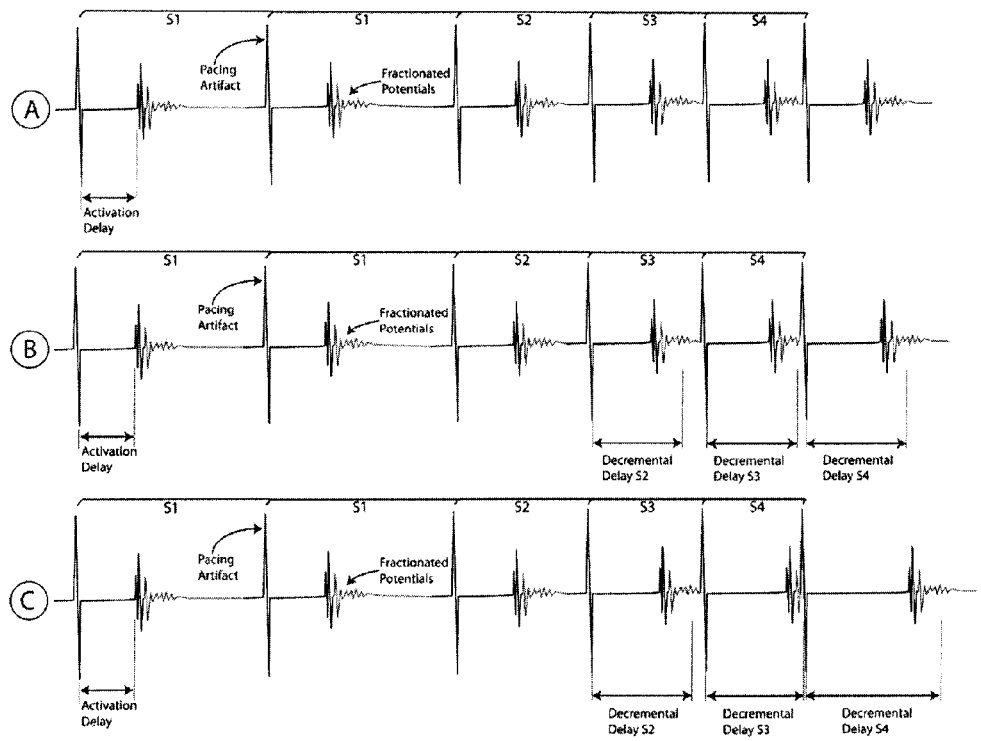
FIG. 18 is a diagram showing fractionated potentials for various positions relative to the exit point of the isthmus.

The recording at position A in FIG. 18 shows fractionated potentials at the exit point of the isthmus. Decrementing Sx interval results in a similar pattern of activation, indicating absence of a conduction block. Position B is located at the entry point of the isthmus and the potentials get delayed as shown in the recording labeled B. Position C is located in the isthmus close to the conduction block area and it shows maximum delay, confirming the close presence of the conduction block in the circuit. The objective of the DEEP mapping procedure described herein is to locate the point where this delay is maximized and identify an adjacent area where there is no or minimal delay.

Figure 19:
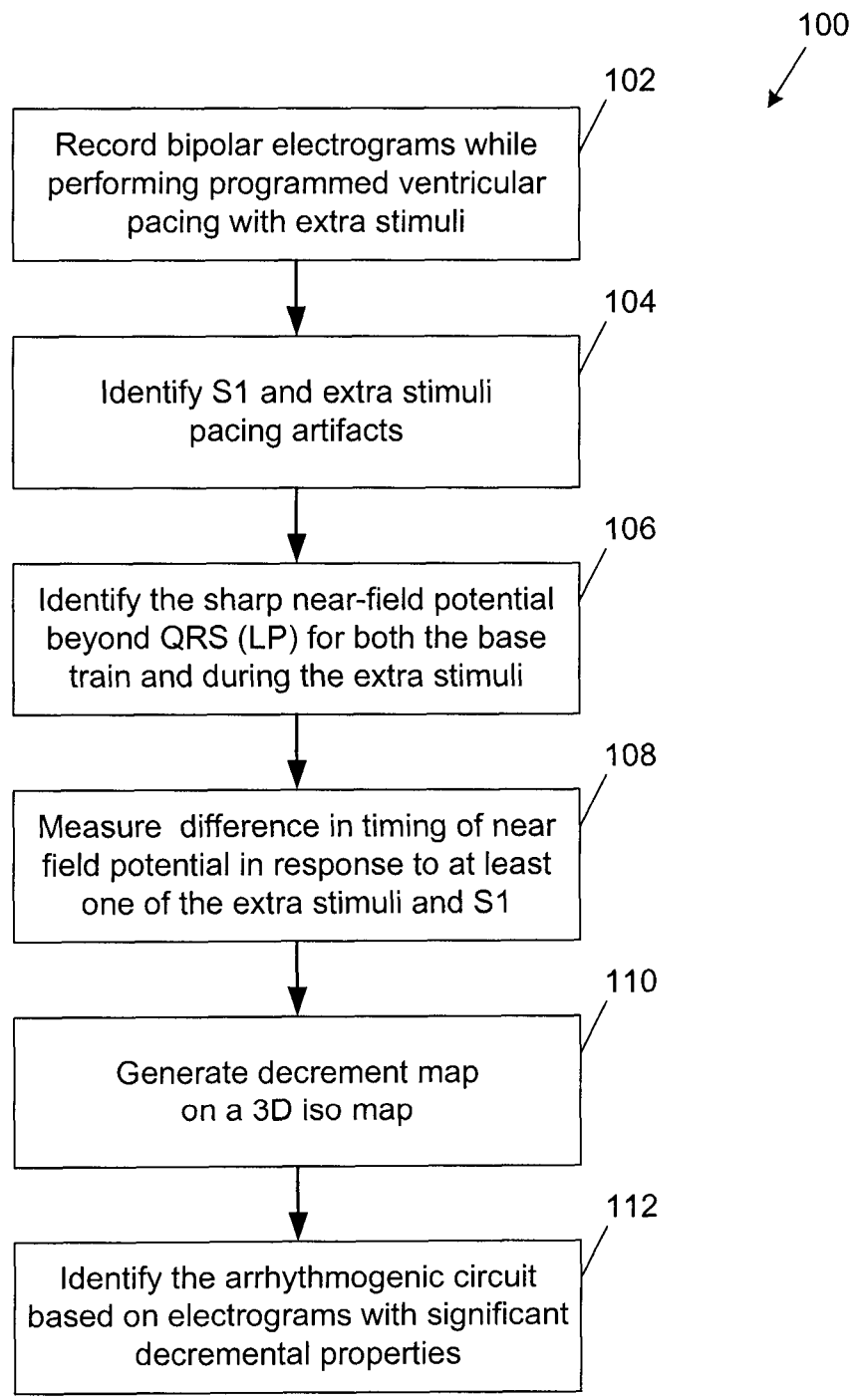
FIG. 19 is a flowchart of an example embodiment of a method that can be used to perform Decrement EvokEd Potential (DEEP) mapping to identify components of the arrythmogenic circuit in cardiac arrhythmias.

The DEEP mapping technique described herein is catheter agnostic. Accordingly, the DEEP mapping technique can be used with a standard multi-electrode catheter, a single electrode catheter or a device that employs a small number of electrodes such as 4 for example, a non-contact mapping array that uses an inverse solution, a multi-splined multi-electrode, or a non-invasive surface mapping tool. The DEEP mapping method described herein may also be used with a conventional electrical stimulator with a decremental protocol to stimulate the cardiac system of a patient or subject. Electrograms are analyzed using the DEEP mapping module 34, which is custom software that implements the DEEP mapping method, an example of which is shown in FIG. 19, to identify the VT exit point. Ablation can later be performed at the VT exit point using appropriate techniques (e.g. RF, cryo-ablation and the like).

Referring now to FIG. 19, shown therein is a flowchart of an example embodiment of a DEEP mapping method 100 that can be used to identify components of the arrythmogenic circuit in cardiac arrhythmias.

At 102, the DEEP mapping method 100 comprises recording electrograms with a cardiac mapping system while performing programmed ventricular pacing with extra stimuli. For example, there can be two or three extra stimuli. The potentials may be measured such that the electrograms may be bipolar electrograms, unipolar electrograms or virtual electrograms. The cardiac mapping system can be the system 10 which uses the stimulation unit 44 to provide the stimuli to the heart of a patient or a subject and the sensor unit 42 to record the signals that make up the bipolar electrograms at various locations in the heart. Alternatively, other mapping systems or components thereof that can provide the required functionality may be used. For example, in some cases, the stimulation unit 44 can be an ablation unit.

At 104, the DEEP mapping method 100 comprises identifying the S1 and at least the S2 pacing artifacts in at least two of the recorded electrograms that correspond to different locations of the heart. In one example embodiment, this can be done using an output sync signal from the stimulation unit 44 as well as using the activation detection method shown in FIG. 3. In alternative embodiments, other extra stimuli may also be used such as, but not limited to, S3, for example. In some cases it may be possible to use S3 and S4 as long as the risk of inducing VT is not increased.

Figure 20:
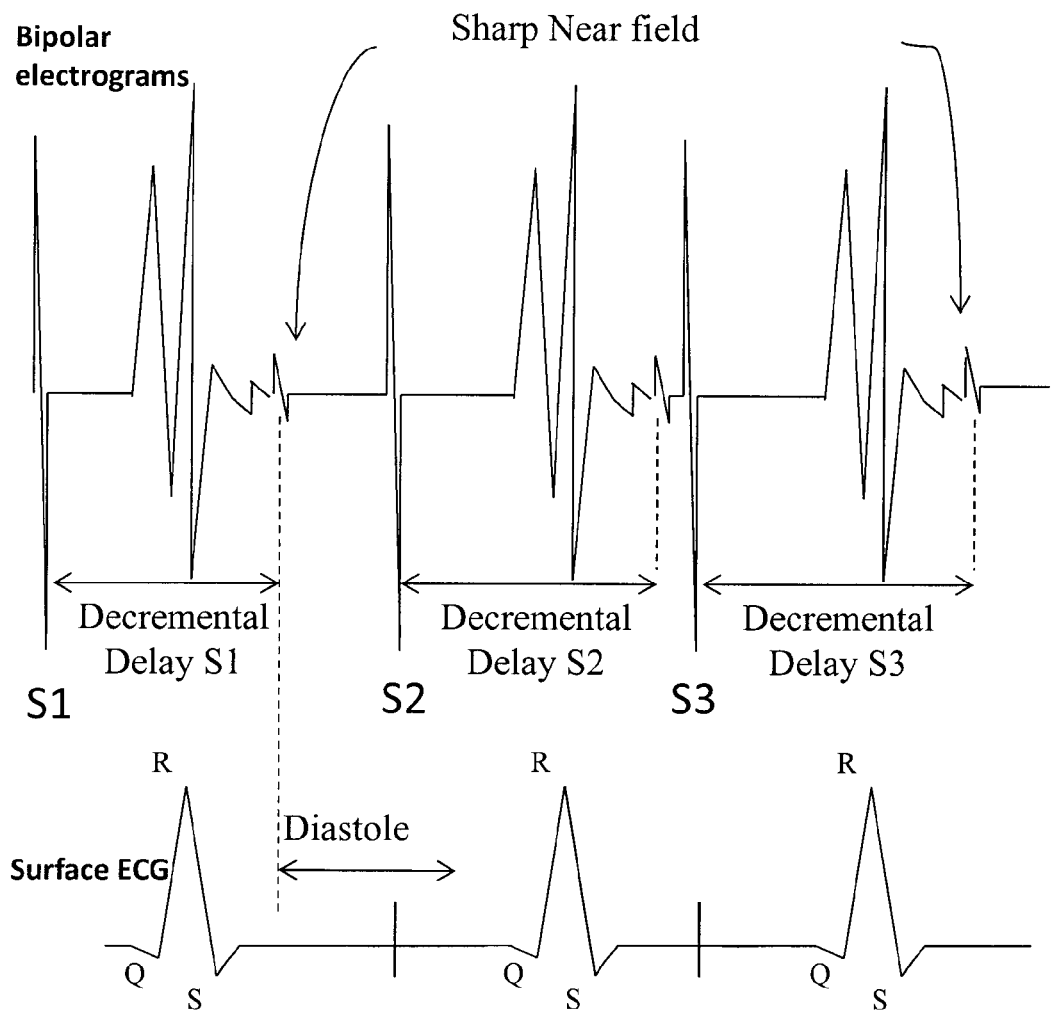
FIG. 20 is a diagram illustrating the latest sharp near field and the surface ECG during the electrode recordings taken for performing DEEP mapping.

At 106, the DEEP mapping method 100 comprises identifying the sharp near-field potential beyond the QRS complex (i.e. LP) for both the base train (S1) and during extra beats (at least S2). The near-field sharp potential may be identified based on the time-derivative of the potential (dV/dT), such as, for example, the potential with the most negative dV/dT value. FIG. 20 is an illustration of sharp near field potentials that can occur outside the QRS complex or in other words during diastole. FIG. 20 also illustrates the decremental delay as a result of the stress induced on the myocardium by the tightly coupled extra-stimuli.

At 108, the DEEP mapping method 100 comprises measuring the difference in timing of the LP in response to the extra stimuli with respect to S1 to obtain decrement values. For example, for S2, or for S2 and S3, the response may be identified using S1 signal decomposition in which multi-components are identified and the latest component is tracked along the S2 and S3 intervals. For any given extra-stimulus, the timing of the latest potential is recorded.

It should be noted that the ECG signals may be recorded using a multi-electrode sensor unit or a single electrode sensor unit. If the ECG signals are recorded using a multi-electrode sensor unit such as, but not limited to, a non-contact array, multi-spline multi-electrode array, or a non-invasive surface mapping tool, for example, then the decrement values can be obtained for a plurality of different locations, possibly over the whole heart, in a short duration and the method 100 proceeds to 110. Alternatively, if the ECG signals are being recorded using a sensor unit having a single electrode or a small number of electrodes, e.g. by using a roving catheter, then acts 102 to 108 are repeated as the catheter is moved to various locations of the heart and the corresponding decrement values are recorded until a sufficient number of decrement values are measured. In both cases, about 100 decrement values may be sufficient depending on the size of the heart and possibly its condition. In other cases, the number of values may be increased. For example, the number of values that are used may be determined on the proportion of the heart that is unhealthy and the desired resolution. For example, in some cases, the number of locations may be as much as 250 or 400.

At 110, the DEEP mapping method 100 comprises generating a decrement map. This map may be generated on a 3D iso map for example. In alternative embodiments, it may be possible to generate only a portion of the decrement map that provides the needed information on the arrythmogenic circuit. In further alternative embodiments, it may be possible to generate a 3D map using fixed geometry or a 3D map using anatomical geometry (such as what is shown in FIG. 22, for example).

At 112, the DEEP mapping method 100 comprises identifying the arrhythmogenic circuit based on electrograms that have significant decremental properties, such as a maximum local decrement or other decrements that may be identified by comparison with a threshold determined through experimental or simulation work. In some embodiments, this may be done by using decrement values and gradients of decrement values, where large decrement sites and very small or no decrement sites are spatially adjacent to one another. This may correspond to repeating act 108 until the longest delay is found. In this process, a bystander can be eliminated due to the absence of late potentials. The area of the heart that is found having the longest delay corresponds to position C in FIG. 17, i.e. near a unidirectional block.

It should be noted that FIG. 19 and the corresponding description provide one example embodiment for performing DEEP mapping and that other alternative embodiments can be used. For example, in at least one embodiment the DEEP mapping method may comprise obtaining data for electrograms recorded at various locations of the heart while programmed ventricular pacing with extra stimuli was performed; identifying a sharp near-field potential beyond a QRS complex for both a base train and the extra stimuli for at least two of the recorded electrograms; obtaining decrement values for at least two different locations of the heart based on measuring a time difference of the near-field potential in response to the extra stimuli and the time difference between the near-field potential in response to the base train in the at least two recorded electrograms corresponding to the different locations of the heart; generating at least a portion of a decrement map using the decrement values; and identifying the arrhythmogenic circuit based on electrograms having significant decremental properties.

It should be noted that obtaining data for recorded electrograms at various locations means that the data may be directly recorded by the system 10. Alternatively, the data for the recorded electrograms may have been previously acquired and is stored in a data store in which case obtaining the data for the recorded electrograms means accessing the data from the data store.

In general, a given decrement value may be obtained by subtracting a time delay measured in response to the base train from a time delay measured in response to the extra stimuli.

In at least one embodiment, the base train and the extra stimuli may comprise S2. In other embodiments, the extra stimuli may comprise S2 and S3.

In at least one embodiment, the sharp near-field potential is identified beyond the QRS complex for both the base train and the extra stimuli.

In at least one embodiment, the DEEP mapping method may comprise obtaining decrement values for various locations of the heart by measuring a time difference of the LP in response to at least one of the extra stimuli with respect to the stimuli S1 in the at least two recorded electrograms corresponding to the different locations of the heart.

In at least one embodiment, before identifying the near sharp field potential, the DEEP mapping method may comprise identifying S1 and extra stimuli pacing artifacts in the recorded electrograms.

In at least one embodiment, the DEEP mapping method comprises recording one of bipolar electrograms, unipolar electrograms and virtual electrograms.

In at least one embodiment, the DEEP mapping method may further comprise identifying significant decremental properties by using decrement values of the decrement map and/or spatial gradients of the decrement values.

In at least one embodiment, the DEEP mapping method may further comprise obtaining decrement values until a largest decrement value is obtained indicating a longest delay.

In at least one embodiment, one or more unidirectional blocks may be located by finding one or more regions on the decrement map with long decrement that are adjacent to one or more regions that have short decrement (thereby determining decrement spatial gradients). Areas of unidirectional block may be seen where these DEEP spatial gradients are present.

In at least one embodiment, the electrograms may be recorded using a multi-electrode array sensor to obtain the electrograms for a plurality of locations of the heart in a short duration. In these cases, the multi-electrode array sensor may comprise one of an endocardial balloon or a basket electrode array.

Alternatively, in at least one embodiment, the electrograms may be recorded using a sensor unit having a small number of electrodes and moving the sensor unit to various locations of the heart. In these cases, the sensor unit may comprise a roving catheter.

The electrograms may be recorded in an operating room or a cath lab.

The electrograms may be recorded for at least one of a ventricular region, an atrial region, an endocardial region and an epicardial region of the heart.

It should be noted that in alternative embodiments, after DEEP mapping is performed, entrainment may be used to validate the mapping result and confirm that the located position (e.g. position A shown in FIG. 17) corresponds to the exit site.

It should be noted that in alternative embodiments, after DEEP mapping is performed, there may be an additional act in which, for the identified arrhythmogenic circuit, the tissue found between a point with a high decremental value and a point with low decremental value is ablated. Program stimulation may then be used to confirm that the VT is not re-inducible.

It is proposed that the information on the functional decremental conduction properties of scarred areas may add important information in order to gain further understanding of the pathological slow conduction that is frequently seen during VT diastole. As such the DEEP mapping method described herein has the potential to guide ablation specifically those sites and may enhance the efficacy of catheter ablation. All ablation in the ventricles carries the obvious risk of causing collateral damage to cardiac structures such as the conduction system, valves and coronary vessels in addition to direct trauma from the catheter and lesion formation such as thromboembolism or cardiac perforation. Even though not frequently reported, ablation over areas of relatively healthy myocardium may theoretically cause reduction in the already depressed ventricular function. Therefore, a focused lesion set at critical areas for VT maintenance may be sought in order to minimize the risk of complications and maximize the efficacy of the procedure. Mapping potential targets with DEEP may be more specific than the standard methods of mapping due to the addition information of functional properties when the pathological myocardium is stressed by tightly coupled extra-systoles.

One of the strengths of decremental functional mapping, i.e. the DEEP mapping method described herein, is the substrate-based approach used to identify the site of the critical component of VT without the strict need for documented or inducible tachycardia. It is believed that DEEP mapping, as described herein, by virtue of identifying areas of slow conduction, may have the potential to improve the efficacy and safety of VT ablation in patients with substrate-based arrhythmias. It is also believed that DEEP mapping, as described herein, may allow for identifying the critical component of Atrial Tachycardia (AT) without induction of atrial tachycardia in congenital atrial arrhythmias. It is also believed that DEEP mapping, as described herein, may allow for identifying the site of the critical component of Ventricular Fibrillation (VF) without induction of VF.

In another aspect, the DEEP mapping technique described herein may be used to identify the site of critical components of AT. In this case, the stimulation site is now located in the atria and the number of points where data is recorded may be reduced since the atrias are smaller than the ventricles.

In another aspect, the DEEP mapping technique described herein may be used to identify the site at which initiating rotors of Atrial Fibrillation (AF) locate themselves. This involves an equal manifestation for surface P wave instead of the QRS complex. Once again, in this case, the stimulation site is now located in the atria and the number of points where data is recorded may be reduced since the atrias are smaller than the ventricles.

In another aspect, the DEEP mapping technique described herein may be used to identify regions that are vital in maintaining arrhythmias in the heart without induction of arrhythmia when it is too dangerous to induce the arrhythmia as well as in situations where arrhythmia cannot be induced in the operating room due to sedation and other non-inducibility issues.

In another aspect, the DEEP mapping technique described herein can be used as a guide for certain cardiac procedures, such as VT ablation procedures. The DEEP mapping technique interrogates and predicts the physiological pathways that maintain VT, without the need for activation mapping during VT as it probes the substrate responsible for the arrhythmia. Accordingly, the DEEP mapping method may be more likely to identify only the regions of importance in the VT circuit that would result in successful outcome of a subsequent cardiac ablation procedure and also provide a mechanistic insight of the tachycardia.

It should be noted that the DEEP mapping method has been observed to work in the operating room as well as in the cath lab.

It should also be noted that the DEEP mapping method has been observed to work for various forms of cardiomyopathy including ischemic cardiomyopathy, dilated cardiomyopathy, and congenital diseased hearts.

It should also be noted that the DEEP mapping method has been observed to work when mapping the endocardium and the epicardium.

It should also be noted that a hypothesis that was tested in the study was that slow conduction, decrement precedes block and re-entry. Since this study involved data from the clinical setting, the definition of slow decremental conduction and unidirectional block is derived from: (a) wave front activation pattern and (b) bipolar signal morphology changes. This is much in keeping with data from the clinical study of atrioventricular nodal reciprocating tachycardia and fascicular tachycardia, which share the features of re-entry with ischemic ventricular tachycardia. Furthermore, activation from the other direction will flip the axis of the local electrogram and morphology and bidirectional blocked regions do not maintain reentry and do not demonstrate this phenomenon.

Furthermore, it was considered that if a cardiac potential takes a longer time to arrive at a given site with extra-beat stimuli then: (1) it may be due to a block occurring at fibers conducting at baseline, forcing the electrical activation to occur via alternative pathways, or (2) it may be a true decrement occurring at the cellular level. It may not be possible to obtain evidence that one of these models is valid over the other and it may also be the case that a combination of these models may be occurring. Either way, the net result is a decremental pattern of activation that is: (a) progressive with an increasing number of extra beats, (b) frequently causing unidirectional block (at least functionally) and (c) resulting in re-entrant tachycardia.

It is further believed that the DEEP mapping method may work in any substrate that involves decremental conduction, uni-directional block and re-entry and where the mapping is of sufficient density. For instance, the arrhythmia seen in Dilated Cardiomyopathy (DCM) and Arrhythmogenic Right Ventricular Cardiomyopathy (ARVC) is frequently re-entrant and therefore shares the main attribute from cases studied using DEEP mapping. Also fascicular tachycardia is very frequently re-entrant and relies on slowly conducting tissue, and theoretically may be mapped with the DEEP method given sufficient electrode density. However, there are some differences that may be important including scar heterogeneity that might be greater in DCM and have quite a different location (e.g. epicardium as opposed to the endocardium). The DEEP mapping method may also be suitable for atrial arrhythmias involving re-entry, including typical atrial flutter, scar-related atrial tachycardia and atrial fibrillation.

It should be noted that although 112 electrodes were used to collect the data in the study described herein, the strength of the data was not due to the spatial density of the resulting mapping, but rather the simultaneous nature of the data used for the mapping. Furthermore, while the spacing of the bipoles (e.g. 1 mm) and the physical location of the electrodes impose spatial constraints on the density of mapping, a higher density of data due to the use of more electrodes should result in more detailed maps of the decremental areas.

At least some of the elements of the system 10 that are implemented via software may be written in a high-level procedural language such as object oriented programming and/or a scripting language. Accordingly, the program code may be written in C, C++, MATLAB, JAVA, SQL or any other suitable programming language and may comprise modules or classes, as is known to those skilled in object oriented programming. Alternatively, or in addition thereto, some of the elements of the system 10 that are implemented via software may be written in assembly language, machine language or firmware as needed. In either case, the language may be a compiled or an interpreted language.

At least some of the program code can be stored on a storage media (e.g. a computer readable medium such as, but not limited to, ROM, a magnetic disk, an optical disc and the like) or a device that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the components described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, USB keys, external hard drives and magnetic and electronic storage. In alternative embodiments, the medium may be transitory in nature such as, but not limited to, wire-line transmissions, satellite transmissions, Internet transmissions or downloads, digital and analog signals, and the like. The computer useable instructions may also be in various forms, including compiled and non-compiled code.

Various embodiments of systems, processes and devices have been described herein by way of example only. Various modifications and variations may be made to these example embodiments without departing from the spirit and scope of the embodiments, which is limited only by the appended claims. It is not intended that the applicant's teachings be limited to such embodiments. On the contrary, the applicant's teachings described and illustrated herein encompass various alternatives, modifications, and equivalents, and the appended claims should be given the broadest interpretation consistent with the description as a whole.

REFERENCES

[R1.1] D. Durrer, R. Th. Van Dam, G. E. Freud, M. J. Janse, F. L. Meijler, and R. C. Arzbaecher, "Total Excitation of the Isolated Heart", Circulation, Vol. 16, pp. 899-912, 1970.

[R1.2] I. D. Parson, and E. Downar, "Cardiac Mapping Instrumentation for the Instantaneous Display of Endocardial and Epicardial Activation", IEEE Trans. Biomed. Eng., Vol. BME-34, No. 6, pp. 468-472, 1987.

[R1.3] R. E. Ideker, W. M. Smith, S. M. Blanchard, S. L. Reiser, E. V. Simpson, P. D. Wolf, and N. D. Danieley, "The Assumptions of Isochronal Cardiac Mapping", Pace, Vol. 12, pp. 456-478, 1989.

[R1.4] I. D. Parson, P. Mendler, and E. Downar, "On-Line Cardiac Mapping: An Analog Approach using Video and Multiplexing Techniques", Am. J. Physiol., No. 242, pp. H526-H535, 1982.

[R1.5] R. E. Ideker, W. M. Smith, P. Wolf, N. D. Danieley, and F. R. Bartram, "Simultaneous Multichannel Cardiac Mapping Systems", Pace, Vol. 10, pp. 281-292, 1987.

[R1.6] S. Masse, E. Sevaptsidis, I. D. Parson, S. Kimber, and E. Downar, "A Data Acquisition System for Real-Time Activation Detection of Cardiac Electrograms II: Software", submitted to the 13th Annual International Conference of the IEEE Engineering in Medicine and Biology Society, 1991, pp. 782-783.

[R2.1] S. Masse, E. Sevaptsidis, I. D. Parson, S. Kimber, and E. Downar, "A Data Acquisition System for Real-Time Activation Detection of Cardiac Electrograms I: Hardware", submitted to the 13th Annual International Conference of the IEEE Engineering in Medicine and Biology Society, 1991, pp. 780-781.

[R2.2] S. M. Blanchard, W. M. Smith, R. J. Damiano, D. W. Molter, R. E. Ideker, and J. E. Lowe, "Four Digital Algorithms for Activation Detection from Unipolar Epicardial Electrograms", IEEE Trans. Biomed. Eng., vol. BME-36, No. 2, pp. 256-261, 1989.

[R2.3] C. Cabo, J. M. Wharton, R. E. Ideker and W. M. Smith, "Digital Filters for Activation Detection in Unipolar Cardiac Electrograms", 10th Annual International Conference of the IEEE Engineering in Medicine and Biology Society, p. 0110, 1988.

[R2.4] E. V. Simpson, R. E. Ideker and W. M. Smith, "An Automatic Activation Detector for Bipolar Cardiac Electrograms", 10th Annual International Conference of the IEEE Engineering in Medicine & Biology Society, p. 0113, 1988.

[R2.5] I. D. Parson, P. Mendler, and E. Downar, "On-Line Cardiac Mapping: An Analog Approach using Video and Multiplexing Techniques", Am. J. Physiol., No. 242, pp. H526-H535, 1982.

[R3.1] Natale A, Raviele A, Al-Ahmad A, Alfieri O, Aliot E, Almendral J, Breithardt G, Brugada J, Calkins H, Callans D et al: Venice Chart International Consensus document on ventricular tachycardia/ventricular fibrillation ablation. J Cardiovasc Electrophysiol 2010, 21(3), pp. 339-379.

[R3.2] Carbucicchio C, Santamaria M, Trevisi N, Maccabelli G, Giraldi F, Fassini G, Riva S, Moltrasio M, Cireddu M, Veglia F et al: Catheter ablation for the treatment of electrical storm in patients with implantable cardioverter-defibrillators: short- and long-term outcomes in a prospective single-center study. Circulation 2008, 117(4), pp. 462-469.

[R3.3] Kottkamp H, Wetzel U, Schirdewahn P, Dorszewski A, Gerds-Li J H, Carbucicchio C, Kobza R, Hindricks G: Catheter ablation of ventricular tachycardia in remote myocardial infarction: substrate description guiding placement of individual linear lesions targeting noninducibility. J Cardiovasc Electrophysiol 2003, 14(7), pp. 675-681.

[R3.4] Jais P, Maury P, Khairy P, Sacher F, Nault I, Komatsu Y, Hocini M, Forclaz A, Jadidi A S, Weerasooryia R et al: Elimination of local abnormal ventricular activities: a new end point for substrate modification in patients with scar-related ventricular tachycardia. Circulation 2012, 125(18), pp. 2184-2196.

[R3.5] Arenal A, Glez-Torrecilla E, Ortiz M, Villacastin J, Fdez-Portales J, Sousa E, del Castillo S, Perez de Isla L, Jimenez J, Almendral J: Ablation of electrograms with an isolated, delayed component as treatment of unmappable monomorphic ventricular tachycardias in patients with structural heart disease. J Am Coll Cardiol 2003, 41(1), pp. 81-92.

[R3.6] Yokokawa M, Desjardins B, Crawford T, Good E, Morady F, Bogun F: Reasons for recurrent ventricular tachycardia after catheter ablation of post-infarction ventricular tachycardia. J Am Coll Cardiol 2013, 61(1), pp. 66-73.

[R3.7] Yoshida K, Sekiguchi Y, Tanoue K, Endo M, Suzuki A, Kanemoto M, Yamasaki H, Yamauchi Y, Takahashi A, Kuga K et al: Feasibility of targeting catheter ablation to the markedly low-voltage area surrounding infarct scars in patients with post-infarction ventricular tachycardia. Circ J 2008, 72(7), pp. 1112-1119.

[R3.8] Mickleborough L L, Harris L, Downar E, Parson I, Gray G: A new intraoperative approach for endocardial mapping of ventricular tachycardia. J Thorac Cardiovasc Surg 1988, 95(2), pp. 271-280.

[R3.9] Mickleborough L L, Usui A, Downar E, Harris L, Parson I, Gray G: Transatrial balloon technique for activation mapping during operations for recurrent ventricular tachycardia. J Thorac Cardiovasc Surg 1990, 99(2), pp. 227-232; discussion pp. 232-223.

[R3.10] Mickleborough L L, Mizuno S, Downar E, Gray G C: Late results of operation for ventricular tachycardia. Ann Thorac Surg 1992, 54(5), pp. 832-838; discussion pp. 838-839.

[R3.11] Greenberg S M, Epstein A E, Deering T, Goldman D S, Ghidina M, Neason C, Proclemer A: A Comparison of ICD implantations in the United States versus Italy. Pacing Clin Electrophysiol 2007, 30 Suppl 1:S143-146.

[R3.12] Ng A C, Bertini M, Borleffs C J, Delgado V, Boersma E, Piers S R, Thijssen J, Nucifora G, Shanks M, Ewe S H et al: Predictors of death and occurrence of appropriate implantable defibrillator therapies in patients with ischemic cardiomyopathy. Am J Cardiol 2010, 106 (11), pp. 1566-1573.

[R3.13] Almendral J M, Gottlieb C D, Rosenthal M E, Stamato N J, Buxton A E, Marchlinski F E, Miller J M, Josephson M E: Entrainment of ventricular tachycardia: explanation for surface electrocardiographic phenomena by analysis of electrograms recorded within the tachycardia circuit. Circulation 1988, 77(3), pp. 569-580.

[R3.14] El-Shalakany A, Hadjis T, Papageorgiou P, Monahan K, Epstein L, Josephson M E: Entrainment/ mapping criteria for the prediction of termination of ventricular tachycardia by single radiofrequency lesion in patients with coronary artery disease. *Circulation* 1999, 99(17), pp. 2283-2289.

[R3.15] Segal O R, Chow A W, Markides V, Schilling R J, Peters N S, Davies D W: Long-term results after ablation of infarct-related ventricular tachycardia. *Heart Rhythm* 2005, 2(5), pp. 474-482.

[R3.16] Arenal A, Hernandez J, Calvo D, Ceballos C, Atea L, Datino T, Atienza F, Gonzalez-Torrecilla E, Eidelman G, Miracle A et al: Safety, long-term results, and predictors of recurrence after complete endocardial ventricular tachycardia substrate ablation in patients with previous myocardial infarction. *Am J Cardiol* 2013, 111(4), pp. 499-505.

[R3.17] Kuck K H, Schaumann A, Eckardt L, Willems S, Ventura R, Delacretaz E, Pitschner H F, Kautzner J, Schumacher B, Hansen P S: Catheter ablation of stable ventricular tachycardia before defibrillator implantation in patients with coronary heart disease (VTACH): a multicentre randomised controlled trial. *Lancet* 2010, 375(9708), pp. 31-40.

[R3.18] Tanner H, Hindricks G, Volkmer M, Furniss S, Kuhlkamp V, Lacroix D, C DEC, Almendral J, Caponi D, Kuck K H et al: Catheter ablation of recurrent scar-related ventricular tachycardia using electroanatomical mapping and irrigated ablation technology: results of the prospective multicenter Euro-VT-study. *J Cardiovasc Electrophysiol* 2010, 21(1), pp. 47-53.

[R3.19] Stevenson W G, Wilber D J, Natale A, Jackman W M, Marchlinski F E, Talbert T, Gonzalez M D, Worley S J, Daoud E G, Hwang C et al: Irrigated radiofrequency catheter ablation guided by electroanatomic mapping for recurrent ventricular tachycardia after myocardial infarction: the multicenter thermocool ventricular tachycardia ablation trial. *Circulation* 2008, 118(25), pp. 2773-2782.

[R3.20] Massé S, Sevaptsidis E, Parson I D, Kimber S, Downar E: A Data Acquisition System For Real-time Activation Detection Of Cardiac Electrograms I: Hardware. Engineering in Medicine and Biology Society, 1991. Vol. 13: pp. 780-781.

[R3.21] Massé S, Sevaptsidis E, Parson I D, Kimber S, Downar E: A Data Acquisition System For Real-time Activation Detection Of Cardiac Electrograms II: Hardware. Engineering in Medicine and Biology Society, 1991. Vol. 13: pp. 782-783.

[R3.22] Bella P D, Baratto F, Tsiachris D, Trevisi N, Vergara P, Bisceglia C, Petracca F, Carbucicchio C, Benussi S, Maisano F, Alfieri O, Pappalardo F, Zangrillo A, Maccabelli G, Management of Ventricular Tachycardia in the Setting of a Dedicated Unit for the Treatment of Complex Ventricular Arrhythmias: Long Term Outcome after Ablation, *Circulation* 2013, 127(13): pp. 1359-1368.

The invention claimed is:

1. A method for determining a location of a conduction block of a heart, the method comprising:
   obtaining data for electrograms recorded at various locations of the heart while programmed ventricular pacing with extra stimuli was performed;
   identifying sharp near-field potentials beyond a QRS complex for both a base train and the extra stimuli for at least two of the recorded electrograms;
   obtaining decrement values for at least two different locations of the heart where the decrement value for a given location of the heart is obtained by subtracting a time delay of the sharp near-field potential in response to the base train from a time delay of the sharp near-field potential in response to the extra stimuli in the recorded electrograms corresponding to the given location of the heart;
   generating at least a portion of a decrement map using the decrement values obtained for the different locations of the heart; and
   identifying the location of the conduction block based on electrograms having significant decremental properties by comparing the decrement values obtained for the different locations of the heart with other decrement values or a threshold.

2. The method of claim 1, wherein S1 is the base train and the extra stimuli comprise S2 or S2 and S3, and wherein the sharp near-field potentials are identified beyond the QRS complex for both the base train and the extra stimuli.

3. The method of claim 2, wherein the method comprises obtaining decrement values for various locations of the heart by measuring a largest time difference of the sharp near-field potentials in response to at least one of the extra stimuli with respect to the stimuli S1 in the at least two recorded electrograms corresponding to the different locations of the heart.

4. The method of claim 1, wherein before identifying the sharp near-field potential, the method comprises identifying S1 and extra stimuli pacing artifacts in the recorded electrograms.

5. The method of claim 1, wherein the act of obtaining data for electrograms comprises recording one of bipolar electrograms, unipolar electrograms and virtual electrograms.

6. The method of claim 1, wherein the method further comprises identifying significant decremental properties by using decrement values of the decrement map and spatial gradients of the decrement values.

7. The method of claim 1, wherein the method further comprises obtaining decrement values until a largest decrement value is obtained indicating a longest delay.

8. The method of claim 1, wherein one or more unidirectional blocks are located by finding one or more regions on the decrement map with a long decrement that are adjacent to one or more regions that have a short decrement.

9. The method of claim 1, wherein the generated at least a portion of the decrement map is used as a guide for a subsequent cardiac ablation procedure.

10. The method of claim 1, wherein by the decrement values are corrected to a global decrement in surface ECG signals by subtracting the global decrement from the decrement values.

11. A non-transitory computer readable medium comprising a plurality of instructions that, when executed on a microprocessor of a device, adapt the device to implement a method for determining a location of a conduction block of a heart, wherein the method comprises:
   obtaining data for electrograms recorded at various locations of the heart while programmed ventricular pacing with extra stimuli was performed;
   identifying sharp near-field potentials beyond a QRS complex for both a base train and the extra stimuli for at least two of the recorded electrograms;
   obtaining decrement values for at least two different locations of the heart where the decrement value for a given location of the heart is obtained by subtracting a time delay of the sharp near-field potential in response to the base train from a time delay of the sharp near-field potential in response to the extra stimuli in the recorded electrograms corresponding to the given location of the heart;

generating at least a portion of a decrement map using the decrement values obtained for the different locations of the heart; and identifying the location of the conduction block based on electrograms having significant decremental properties by comparing the decrement values obtained for the different locations of the heart with other decrement values or a threshold.

12. The non-transitory computer readable medium of claim 11, wherein one or more unidirectional blocks are located by finding one or more regions on the decrement map with long decrement that are adjacent to one or more regions that have short decrement.

13. The non-transitory computer readable medium of claim 11, wherein one or more unidirectional blocks are located by finding one or more regions on the decrement map with long decrement that are adjacent to one or more regions that have short decrement.

14. The non-transitory computer readable medium of claim 11, wherein the method further comprises obtaining decrement values until a largest decrement value is obtained indicating a longest delay.

15. A system for determining a location of a conduction block of a heart, the system comprising:

an input for receiving data for electrograms recorded at various locations of the heart while programmed ventricular pacing with extra stimuli was performed; and a processing unit for controlling the system, the processing unit being configured to identify sharp near-field potentials beyond a QRS complex for both a base train and the extra stimuli for at least two of the recorded electrograms; to obtain decrement values for at least two different locations of the heart where the decrement value for a given location of the heart is obtained by subtracting a time delay of the sharp near-field potential in response to the base train a time delay the sharp near-field potential in response to the extra stimuli in the recorded electrograms corresponding to the given location of the heart; to generate at least a portion of a decrement map using the decrement values obtained for the different locations of the heart; and to identify the location of a conduction block based on electrograms having significant decremental properties by comparing the decrement values obtained for the different locations of the heart with other decrement values or a threshold.

16. The system of claim 15, wherein the system further comprises measurement and stimulation hardware coupled the processing unit and the input and configured to apply programmed ventricular pacing with extra stimuli to the various locations of the heart while recording the electrograms.

17. The system of claim 16, wherein the system comprises a multi-electrode array sensor including one of an endocardial balloon or a basket electrode array.

18. The system of claim 16, wherein the system comprises a sensor unit having a small number of electrodes and the sensor unit comprises a roving catheter.

19. The system of claim 15, wherein S1 is the base train and the extra stimuli comprise S2 or S2 and S3.

20. The system of claim 15, wherein the processing unit is configured to identify significant decremental properties by using decrement values of the decrement map and spatial gradients of the decrement values.

21. The system of claim 15, wherein one or more unidirectional blocks are located by finding one or more regions on the decrement map with long decrement that are adjacent to one or more regions that have short decrement.

22. The system of claim 15, wherein the generated at least a portion of the decrement map is used as a guide for a subsequent cardiac ablation procedure.

23. The system of claim 15, wherein the processing unit is configured to obtain decrement values until a largest decrement value is obtained indicating a longest delay.

24. The system of claim 15, wherein the processing unit is configured to correct the decrement values to a global decrement in surface ECG signals by subtracting the global decrement from the decrement values.

* * * * *

UNITED STATES PATENT AND TRADEMARK OFFICE
CERTIFICATE OF CORRECTION

PATENT NO. : 9,662,178 B2
APPLICATION NO. : 14/891843
DATED : May 30, 2017
INVENTOR(S) : Kumaraswamy Nanthakumar, Eugene Downar and Stephane Masse It is certified that error appears in the above-identified patent and that said Letters Patent is hereby corrected as shown below:

In the Claims

Claim 15, Column 29, Line 36, "base train a time delay the sharp" should read -- base train from a time delay of the sharp --

Signed and Sealed this
Thirty-first Day of October, 2017

Joseph Matal
*Performing the Functions and Duties of the
Under Secretary of Commerce for Intellectual Property and
Director of the United States Patent and Trademark Office*